(12) United States Patent
Olsen et al.

(10) Patent No.: US 10,278,808 B2
(45) Date of Patent: May 7, 2019

(54) SURGICAL SUPPORT STRUCTURE

(71) Applicant: REGENTS OF THE UNIVERSITY OF MINNESOTA, Minneapolis, MN (US)

(72) Inventors: Timothy W. Olsen, Atlanta, GA (US); Paul E. Loftness, Gibbon, MN (US); Arthur G. Erdman, New Brighton, MN (US)

(73) Assignees: Emory University, Atlanta, GA (US); University of Minnesota, Minneapolis, MN (US)

(*) Notice: Subject to any disclaimer, the term of this patent is extended or adjusted under 35 U.S.C. 154(b) by 329 days.

(21) Appl. No.: 14/499,404

(22) Filed: Sep. 29, 2014

(65) Prior Publication Data

US 2015/0018806 A1 Jan. 15, 2015

Related U.S. Application Data

(62) Division of application No. 11/502,603, filed on Aug. 9, 2006, now abandoned.

(60) Provisional application No. 60/763,536, filed on Jan. 31, 2006.

(51) Int. Cl.
| | | |
|---|---|---|
| *A61B 18/04* | (2006.01) | |
| *A61F 9/008* | (2006.01) | |
| *A61B 18/20* | (2006.01) | |
| *A61F 2/14* | (2006.01) | |
| *A61F 9/007* | (2006.01) | |
| *A61B 17/00* | (2006.01) | |

(52) U.S. Cl.
CPC ............... *A61F 2/14* (2013.01); *A61B 18/04* (2013.01); *A61B 18/20* (2013.01); *A61F 9/00727* (2013.01); *A61F 9/00821* (2013.01); *A61B 2017/00867* (2013.01)

(58) Field of Classification Search
CPC ........ A61F 2/14; A61F 9/00727; A61F 9/007; A61F 9/0081
USPC ............................................................. 606/4
See application file for complete search history.

(56) References Cited

U.S. PATENT DOCUMENTS

| | | |
|---|---|---|
| 3,927,471 A | 12/1975 | Tricker |
| 4,043,564 A | 8/1977 | White |
| 4,224,934 A | 9/1980 | Scott et al. |

(Continued)

FOREIGN PATENT DOCUMENTS

| | | |
|---|---|---|
| EP | 1447064 A2 | 8/2004 |
| EP | 1986581 B1 | 10/2012 |
| WO | 2007089277 A1 | 8/2007 |

OTHER PUBLICATIONS

Foulds "Current and Potential Uses of Partial Choroidectomy," 97th Deutche Opthalmologische Gesellschaft e.V. (DOG) Annual Meeting 1999, [online]. [archived on Apr. 27, 2002]. Retrieved from the Internet: <http://web.archive.org/web/20020427143501/http://www.dog.org/1999/e-abstract99/218.html>.

(Continued)

*Primary Examiner* — Scott T Luan
(74) *Attorney, Agent, or Firm* — Emory Patent Group

(57) ABSTRACT

This document discusses, among other things, a system for translocating a multilayer patch. The system includes a support structure having a contact surface for bonding to the patch. The support structure has a shape configured to support the patch following separation of the patch from a surrounding tissue.

21 Claims, 16 Drawing Sheets

(56) References Cited

U.S. PATENT DOCUMENTS

| | | |
|---|---|---|
| 5,487,746 A | 1/1996 | Yu et al. |
| 5,527,356 A | 6/1996 | Peyman et al. |
| 5,540,701 A | 7/1996 | Sharkey et al. |
| 5,755,716 A | 5/1998 | Garito et al. |
| 5,817,075 A | 10/1998 | Giungo |
| 5,847,746 A | 12/1998 | Takahashi |
| 5,962,027 A * | 10/1999 | Hughes ............ A61B 19/00 424/422 |
| 6,015,417 A | 1/2000 | Reynolds, Jr. |
| 6,036,678 A | 3/2000 | Giungo |
| 6,045,791 A | 4/2000 | Liu |
| 6,156,042 A | 12/2000 | Aramant |
| 6,159,218 A | 12/2000 | Aramant et al. |
| 6,165,042 A | 12/2000 | Chin |
| 6,193,732 B1 | 2/2001 | Frantzen et al. |
| 6,398,797 B2 * | 6/2002 | Bombard ............ A61B 17/064 227/175.1 |
| 6,402,765 B1 | 6/2002 | Monassevitch et al. |
| 6,514,238 B1 * | 2/2003 | Hughes .............. A61F 2/14 604/239 |
| 6,896,684 B2 | 5/2005 | Monassevitch et al. |
| 6,955,809 B2 | 10/2005 | Hughes |
| 9,539,082 B2 | 1/2017 | Olsen et al. |
| 2003/0054023 A1 | 3/2003 | Hughes |
| 2003/0104618 A1 | 6/2003 | Hughes |
| 2003/0105456 A1 | 6/2003 | Lin |
| 2004/0039401 A1 | 2/2004 | Chow et al. |
| 2004/0254567 A1 * | 12/2004 | Holz ............... A61F 9/008 606/4 |
| 2005/0038460 A1 | 2/2005 | Jayaraman |
| 2005/0251154 A1 | 10/2005 | Chanduszko et al. |
| 2005/0267525 A1 | 12/2005 | Chanduszko |
| 2006/0002900 A1 | 1/2006 | Binder et al. |
| 2006/0039993 A1 | 2/2006 | Hughes |
| 2006/0110428 A1 | 5/2006 | deJuan et al. |
| 2006/0249875 A1 | 11/2006 | Robb et al. |
| 2007/0149989 A1 | 6/2007 | Santilli et al. |
| 2007/0179512 A1 | 8/2007 | Olsen et al. |
| 2009/0118747 A1 | 5/2009 | Bettuchi et al. |
| 2010/0010520 A1 | 1/2010 | Takahashi et al. |
| 2015/0018806 A1 | 1/2015 | Olsen et al. |
| 2015/0223929 A1 | 8/2015 | Olsen et al. |

OTHER PUBLICATIONS

Joussen et al. (Jul. 2006). "Autologous Translocation of the Choroid and Retinal Pigment Epithelium in Age-Related Macular Degeneration," American Journal of Opthalmology, 142(1):17-30.

Stanga et al. (2002). "Retinal Pigment Epithelium Translocation After Choroidal Neovascular Membrane Removal in Age-Related Macular Degeneration," Opthalmology, 109(8): 1492-1498.

Van Meurs et al. (2003). "Autologous Retinal Pigment Epithelium and Choroid Translocation in Patients with Exudative Age-related Macular Degeneration: Short-term Follow-up." American Journal of Opthalmology. 136(4): 688-695.

International Search Report for PCT Application No. PCT/US2006/031177 dated Dec. 27, 2006.

International Preliminary Report on Patentability for PCT Application No. PCT/US2006/031177 dated Aug. 5, 2008.

Written Opinion for PCT Application No. PCT/US2006/031177 dated Jul. 31, 2008.

International Search Report for PCT Application No. PCT/US2010/058090 dated Aug. 19, 2011.

International Preliminary Report on Patentability for PCT Application No. PCT/US2010/058090 dated May 30, 2012.

Written Opinion for PCT Application No. PCT/US2010/058090 dated Aug. 19, 2011.

Communication for EP Application No. 06 801 125.3-2319 dated May 5, 2009.

Response to May 5, 2009 EP Communication for EP Application No. 06 801 125.3-2319 dated Sep. 10, 2009.

Communication for EP Application No. 06 801 125.3-2319 dated Nov. 2, 2010.

Response to Nov. 2, 2010 EP Communication for EP Application No. 06 801 125.3-2319 dated Mar. 3, 2011.

* cited by examiner

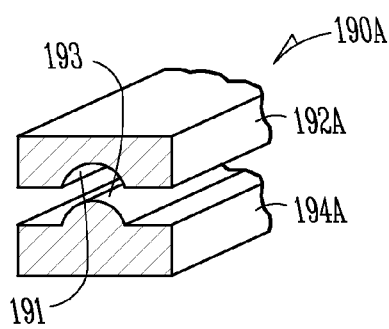
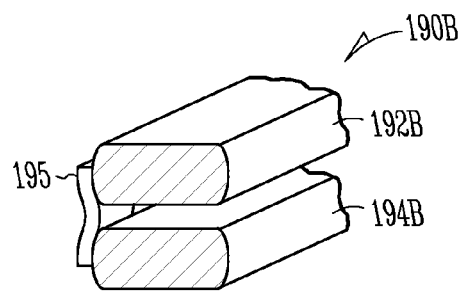
Fig.19A     Fig.19B
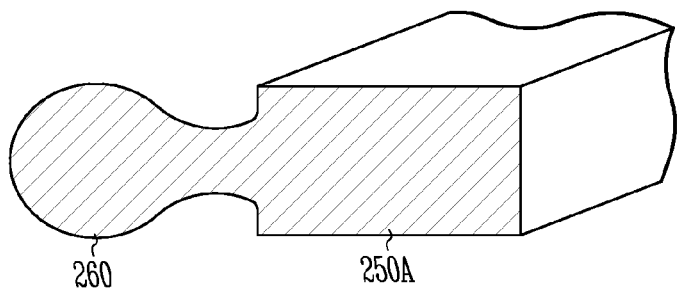
Fig.20A
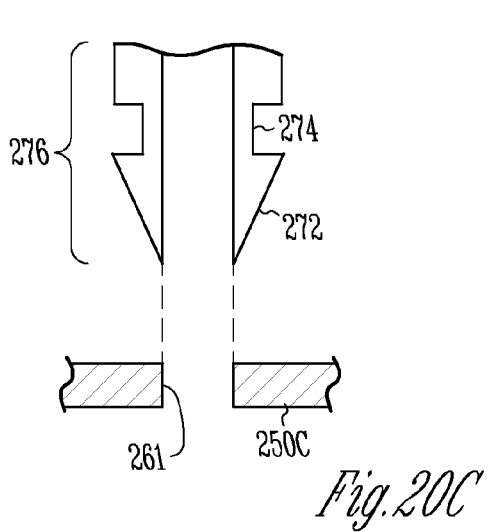
Fig.20C
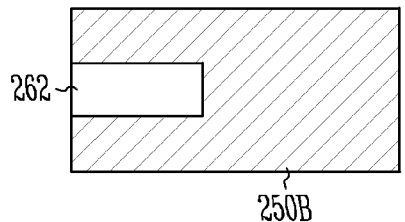
Fig.20B

SURGICAL SUPPORT STRUCTURE

CROSS-REFERENCE TO RELATED APPLICATIONS

This application is a divisional of U.S. patent application Ser. No. 11/502,603, filed on Aug. 9, 2006, pending, which claims the benefit of priority, under 35 U.S.C. Section 119(e), to Timothy W. Olsen et al., U.S. Provisional Patent Application Ser. No. 60/763,536, entitled "SURGICAL SCAFFOLD," filed on Jan. 31, 2006. The applications are hereby incorporated herein by reference in their entireties.

TECHNICAL FIELD

This document pertains generally to ophthalmology, and more particularly, but not by way of limitation, to ophthalmic surgery.

BACKGROUND

Age-related macular degeneration (AMD) is a form of degeneration that results when the delicate photoreceptors deteriorate in a highly specialized region of the central retina called the macula. AMD is the leading cause of visual impairment and blindness for many people over age 50. The cause of AMD is not fully understood, and at present, there is no cure.

AMD is an eye disease of the macula: a tiny area in the retina that helps produce sharp, central vision required for central visual activities such as reading, sewing, and driving. A person with AMD loses this clear, central vision and in some cases, vision loss is rapid and profound. AMD is a leading cause of severe visual impairment and blindness in the United States. According to current statistics, approximately 1.5 million citizens in the United States are affected by advanced age-related macular degeneration. This number is expected to increase to 2.95 million Americans by the year 2020, according to current government statistics.

There are two forms of AMD: an atrophic form, called dry AMD, and an exudative form (eAMD), also called wet AMD. Dry AMD is the early stage of the disease; about 90% of the diagnosed cases of AMD are the dry form, but it is the wet form that results in most of the vision loss associated with the disease. The term AMD is sometimes used to refer only to the advanced form of the disease and the term Age-related Maculopathy (ARM) is used to describe the early clinical findings associated with AMD.

Dry AMD is associated with extracellular deposits called drusen (druse is the singular form of the word but is not commonly used) that form between the retinal pigment epithelium (RPE) and Bruch's membrane. Drusen are believed to result from impaired metabolism in the RPE. In a normal eye, the RPE serves a number of roles critical to healthy vision: renewal of the photoreceptor outer segments through phagocytosis, providing a blood-retinal barrier through the tight junctions between RPE cells, and the selective transport of nutrients across Bruch's membrane to the outer retina. Dry AMD usually results in a gradual loss of central vision in the macular regions associated with the drusen and loss of the RPE.

Wet AMD is also associated with the drusen deposits plus new blood vessel growth or neovascularization. Wet AMD results when fragile blood vessels grow from the choroid into the subretinal space, leaking blood and fluid, and leading to rapid loss of central vision. The growth of new vessels under the retina is called choroidal neovascularization, or CNV. Exudative AMD is a major cause of severe vision loss. Wet AMD is a major cause of severe vision loss and accounts for approximately 80% of such cases. Wet AMD often causes rapid decline in visual acuity.

The eye includes three tissue layers, or tunics as shown in the partial sagittal section of the human eye in FIG. 1. The outermost layer of the eye is fibrous tunic 10 and includes the transparent cornea (near lens 12) and the opaque white sclera. The middle, highly vascularized layer of tissue within the eye is called uveal tract 15. The innermost tunic, or layer, of the eye is retina 20, which is an extension of the central neural tissue of the brain. Retina 20 is comprised of the multi-layered neurosensory retina 22 and a tightly spaced monolayer of hexagonal-shaped cells called the RPE 25 as shown in FIG. 2. Bruch's membrane 35 is a thin, collagenous membrane separating RPE 25 from choroid 30 as shown in FIG. 2. Although RPE 25 must be in close apposition to neurosensory retina 22 for normal visual function, there is only a weak attachment between these two tissue layers. In both pathologic and surgical retinal detachments, neurosensory retina 22 is separated from RPE 25, with RPE 25 adhering to Bruch's membrane 35. In the present subject matter, it is understood that a graft to be harvested following retinal detachment typically includes RPE 25 lying on Bruch's membrane 35 and underlying choroid 30. As one looks directly into the eye, the central region responsible for the greatest visual acuity is called the macula (40), a circular region approximately 5.5 mm in diameter, as shown in FIG. 1. Macula 40 contains the highest concentration of cone photoreceptor cells that are largely responsible for central, sharp vision and color vision. In the figure, macula 40 is shown in the middle of two temporal arcing vessels (trajectories). Macula 40 is responsible for the central 15 to 20 degrees of visual angle. At the center of macula 40 is the fovea, a 1.5 mm diameter region that contains primarily cone cells.

The human eye can be described as a space-variant optical system because the detector elements within retina 20 (photoreceptors 21) vary as a function of position. Photoreceptors 21 convert light energy entering the eye into electrochemical impulses and are often referred to as rods and cones.

Improved systems and methods for addressing AMD as well as other forms of macular disease such as hereditary macular disorders, post-inflammatory diseases, post-traumatic maculopathy, and toxic maculopathy.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIGS. 19A and 19B illustrate sectional views of a support structure.

FIGS. 20A, 20B, and 20C illustrate sectional views of a support structure.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present subject matter includes methods and systems for establishing a new connection between the macula and healthy underlying tissue. Accordingly, following the procedure as described herein, the macula remains nearly in its original location, and a region of damaged, underlying RPE and choroid is replaced by surgically translocating healthy autologous tissue to support the macula. The present subject matter establishes a new connection between the macula and the choroid, Bruch's membrane, and RPE complex. In one example, the macula or other layer of unhealthy tissue is removed followed by translocation of a graft.

The present subject matter includes translocating a patch, or tissue complex, including an underlying layer of full (or partial) thickness choroid, Bruch's membrane, and RPE. The translocation procedure can be used in eyes having the wet or dry forms of AMD. Prior to translocation of the patch, the periphery of the patch is coagulated using a micropulsed diode laser or other method to minimize shrinkage.

Figure 1:
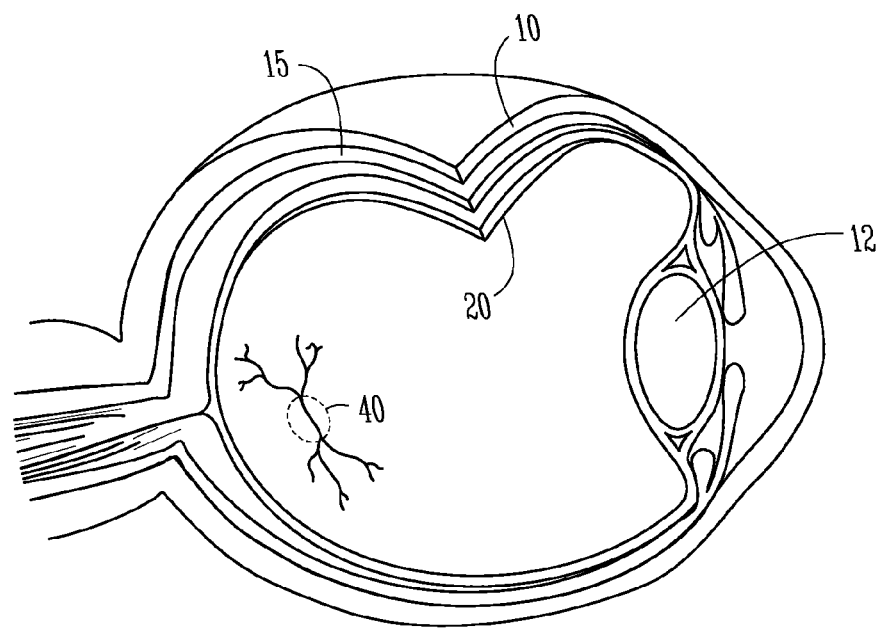
FIG. 1 illustrates a partial sagittal view of an eye.
Figure 2:
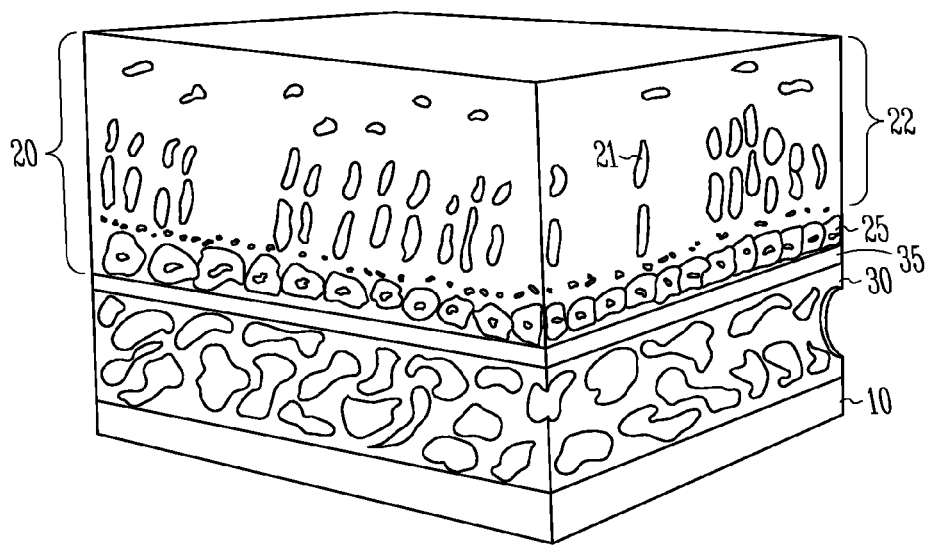
FIG. 2 illustrates a cross-sectional block of the retina, choroid and sclera.

The term tissue refers to any portion of the structure illustrated in FIGS. 1 and 2. The term patch refers to the portion of tissue selected to support the native macular tissue. Accordingly, the patch can be an autograft (including the fellow eye), an allograft (a donor eye), a xenograft (an animal source) or a synthetic graft (generated and grown outside the eye) and describes that portion of tissue selected for translocation. The term patch has meaning at a time before, during and after translocation. According to one example of the present subject matter, the patch is translocated from a first position to a second position. The patch can remain partially attached to the surrounding tissue or can be entirely separated from the surrounding tissue. Portions of this document refer to an autograft however it is understood that other sources of tissue to support the macula are also contemplated, depending upon tissue compatibility and availability.

For example, the tissue, and therefore the patch, can include one or more layers. In one example, the patch includes tissue identified as choroid, Bruch's membrane, and RPE.

In one example, laser energy is used to coagulate the tissue and gain access to the suprachoroidal space for placement of a support structure. The support structure can be viewed as a support frame or support structure for tissue, and in one example, is in the shape of a ring, however other configurations are also contemplated. In some examples, the support structure includes one ring or two rings. In some examples, the support structure includes one or more members each having various shapes and configurations that serve to provide support to the tissue. In one example, the support structure is placed on top of the RPE, and activated by applying energy in order to coagulate and bond to the tissue. In one example, pulsed laser energy from a diode laser is used to create an ablation with minimal shrinkage of surrounding tissue. The donor tissue (patch) can be excised using a knife or other cutting means. The laser method is effective to obtain hemostasis in the vascular choroidal tissues in order to minimize potential bleeding complications from this vascular tissue during excision. Activation of the support structure with electric or radio frequency energy creates coagulation and bonding between individual segments or portions of the support structure and nearby tissue, and with little or no damage to the tissue complex supported by the support structure. In an example where the support structure includes a ring structure, the tissue complex (donor graft) is disposed in the center of the ring. This tissue complex is considered an autograft since it is both harvested from and translocated to the same patient thereby avoiding immune rejection problems.

In various examples, the laser energy is selected to either avoid ablation of the tissue or cause tissue ablation while avoiding excessive tissue shrinkage.

In one example, the intraocular laser has a maximum power level that is insufficient to ablate tissue. Coagulation, in one example, can be performed using a particular laser having a maximum power of 2 W (2,000 milliwatts) and at a distance of 3 mm from probe tip to tissue, the laser can form a region of coagulated tissue of approximately 200 microns wide as the laser probe traces a path at a relatively fixed distance from the support structure. In in vitro testing, a probe tip distance of approximately 2 mm produced good results. Larger or smaller lasers and other parameters are also contemplated.

In one example, a coagulated zone of tissue around the support structure is formed using an 810 nm diode laser in micropulse mode with the endoprobe held 2-3 mm from surface of tissue, a power setting of 750-2,000 milliwatts, a pulse duration of 100 microseconds, and pulse interval ranging from 500 microseconds to 1 millisecond. The coagulated zone is later cut, for example with a diamond knife, to excise the graft.

The coagulated line can be re-traced as needed until a desired burn is achieved. In one example, the laser burn line is repeatedly traced to separate the graft. The surgeon is able to control the burn by altering the rate of travel (distance/time) of the laser probe over the tissue. This control allows for direct surgeon feedback-control of the burn intensity, and allows for variation in choroidal pigmentation. In one example of the present subject matter, the support structure serves as a guide to simplify retracing of the same path.

The present subject matter relates to a support structure that bonds to a surface of tissue. The tissue, according to one procedure, includes choroid and RPE however other tissue is also contemplated. One example of the present subject matter is configured to increase the strength or reinforce the patch to withstand the forces associated with manipulating the patch. In one example, the present subject matter provides support for the patch.

One example of the present subject matter is configured to resist shrinkage and distortion of the excised tissue. The RPE is susceptible to damage if folds are allowed to rub or abrade against each other. In addition, the present subject matter facilitates maintenance of the orientation of the patch. In particular, the patch can be viewed as having a polarity. Maintaining the polarity of the patch can be a factor in the success of the translocation of the patch. The present subject matter can be effective both during and after the separation process.

The support structure includes a contact surface that bonds to the tissue at a target site and counters shrinkage or other distortion after the tissue is separated from the surrounding membrane. The tissue at the target site, after having been excised, is sometimes referred to as a graft. The support structure can have a variety of configurations.

Figure 3:
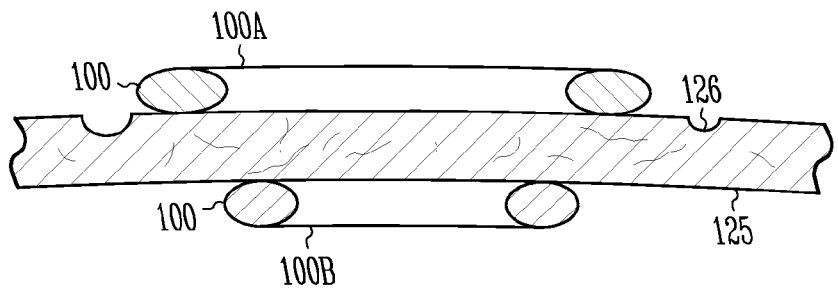
FIG. 3 illustrates a sectional view of a support structure.
Figure 4A:
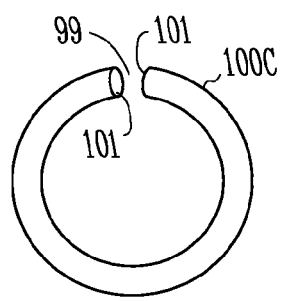
FIGS. 4A-4E illustrate exemplary support structures.
Figure 4B:
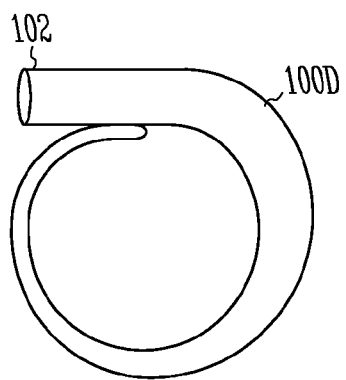

FIG. 3 illustrates a sectional view of an exemplary configuration for the support structure. Support structure 100, which can be considered a reinforcement structure, is shown disposed on opposing surfaces of tissue 125. Support structure 100, in the example illustrated, includes ring 100A and ring 100B. Rings 100A and 100B have a circular configuration and can be endless (or contiguous), or split as illustrated in FIGS. 4A and 4B. In one example, the rings of the support structure have a diameter of 5.5 mm (approximately that of the macula), however, diameters larger or smaller than that of the macula are also contemplated, including, for instance, between 1 and 8 mm. In the figure, rings 100A and 100B have different overall diameters, however, both diameters can be the same. The wire gauge of the rings, in one example, is 175 microns, however, sizes larger or smaller are also contemplated, including, for example a wire diameter of 0.004 inch (approximately 100 microns). In one example, a split ring configuration allows insertion of a portion of support structure 100 through a guide having a length sufficient to preclude unintended penetration of an end of the support structure into the tissue. In one example, a contiguous ring is formed by welding or by cutting from sheet goods. In one example, the guide includes a cannula.

As illustrated in FIG. 4A, ring 100C includes a circular support structure formed of round material. Ring 100C has two ends 101 that are aligned at split 99. In the example illustrated in FIG. 4A, ends 101 lie in the same plane as ring 100C. FIG. 4B illustrates exemplary ring 100D having ends that overlap. Extension 102 protrudes beyond the circular configuration of ring 100D and, in one example, provides a handle or tab by which the support structure can be manipulated, positioned or contacted for purposes of coupling an electrical current or other energy.

In one example, ring 100C includes a shape memory material that returns to a circular configuration as illustrated in the figure, upon warming in response to body temperature. Some shape memory materials have a transition temperature somewhat lower than normal body temperature and are chilled well below body temperature before placement in the body. Ring 100C is shown in a configuration where the temperature is approximately that of the body and, when at a cooler temperature, ring 100C is in the form of a straight wire segment (not shown). As such, ring 100C assumes a circular configuration upon ejection from a cannula using, for example, a pushrod. In one example, ring 100C is formed at the end of a long wire section and is clipped or cut upon ejection from a cannula. In one example, ring 100C separates from the long wire at a notched or weakened segment.

Figure 4C:
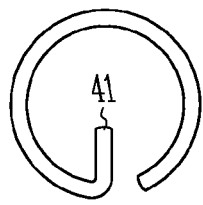
Figure 4D:
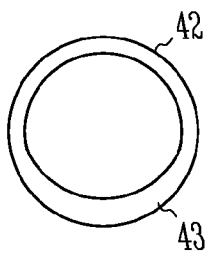
Figure 4E:
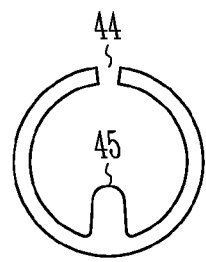

FIGS. 4C, 4D and 4E illustrate alternative embodiments of a support structure with each structure having a feature to facilitate manipulation. In FIG. 4C, the support structure is in the form of a split ring and tab 41 extends from one end of the ring and in a direction towards the interior. A force can be applied to tab 41, for example, to urge the support structure in a direction that increases the contact force on the membrane. In FIG. 4D, the support structure is in the form of an endless ring having a graduated cross section. In particular, portion 42 has a narrower cross section relative to that of portion 43. As with the structure of FIG. 4C, the gradient (or non-uniform section) shown in FIG. 4D allows an operator to control the contact force between the support structure and the membrane. In FIG. 4E, the support structure is in the form of a split ring having tab 45 extending towards the interior of the ring and at a point opposite that of split 44. Tab 45 allows an operator to manipulate the support structure and adjust the contact force on the membrane. In one example, the tab extends outward from the diameter of the ring.

Figure 5:
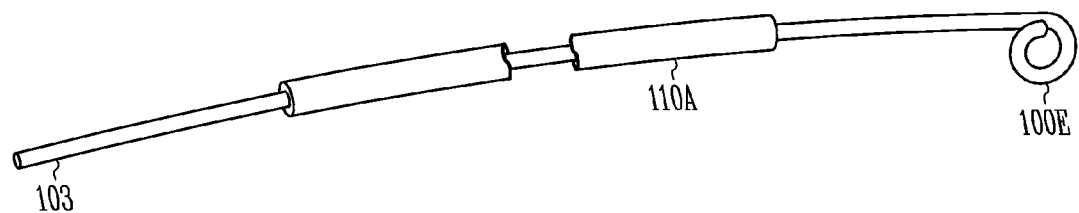
FIG. 5 illustrates a support structure with an insertion guide.

FIG. 5 illustrates support structure 100E coupled to wire 103 disposed in a lumen of guide 110A. Support structure 100E includes a circular configured ring having overlapping ends. Support structure 100E is formed at one end of wire 103. The second end of wire 103 extends beyond guide 110A and allows manipulation of support structure 100E. In addition, electrical energy or other energy can be applied to support structure 100E by coupling with wire 103. In one example, support structure 100E is separated or detached from wire 103 by cutting, breaking or other forms of device disengagement.

Figure 6A:
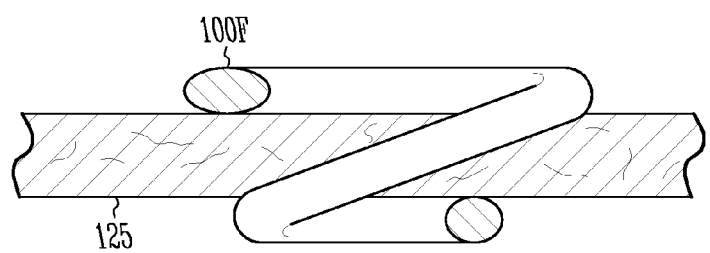
FIGS. 6A and 6B illustrate helical support structures.
Figure 6B:
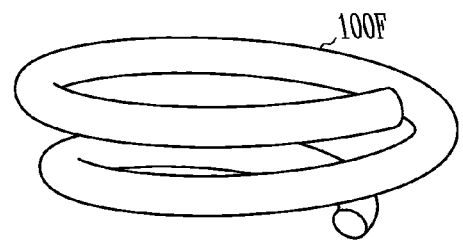

FIG. 6A illustrates a partial sectional view of exemplary support structure 100F in contact with tissue 125. In the figure, a portion of support structure 100F is shown in section using a cut plane that lies parallel to the cut plane of tissue 125. Support structure 100F includes a helical structure and the figure illustrates one portion of a first winding in contact with a first surface of tissue 125 and one portion of a second winding in contact with a second surface of tissue 125. FIG. 6B illustrates a perspective view of support structure 100F without the tissue. Support structure 100F includes circular configured windings with one winding (ring) larger than another winding, however both rings can be of similar or the same size. In one example, the ends of support structure 100F overlap. In one example, the ends of support structure 110F butt together as in the form of a split ring.

In one example, a helical structure includes an electrical resistance element or other structure that allows use of electric resistance heating to bond the support structure to the tissue. In one example, the rings of the support structure can be attached together at a hinge rather than a winding, where both rings can be deployed simultaneously.

In one example, two rings of a support structure can be deployed simultaneously through a delivery system. The rings can be hinged together or otherwise connected. For example, two rings can be coupled together at a pivot point thus allowing them to swing open or clamp closed around tissue. In one example, the two rings are deployed together through a common sheath or insertion element, for example as shown in FIG. 12.

Figure 7:
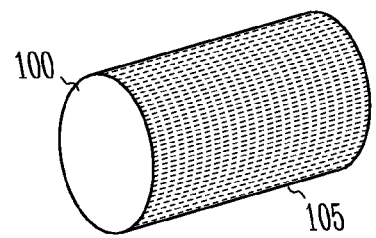
FIG. 7 illustrates a support structure with a particular surface finish.

FIG. 7 illustrates a perspective view of a segment of support structure 100. In various examples, surface 105 of support structure 100 is textured or roughened to enhance bonding to tissue 125 (not shown). Surface 105 can include raised or indented details that increase the surface area of support structure 100. In one example, surface 105 includes a coating or conformal layer having properties that enhance bonding, administer a drug, peptide, growth factor, chemical or other bioactive compound, provide insulation, increase electrical conductivity, or achieve another desirable result. In one example, surface 105 includes a drug eluting coating.

Figure 8A:
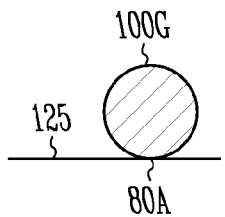
FIGS. 8A, 8B and 8C illustrate sectional views of exemplary support structures.
Figure 8B:
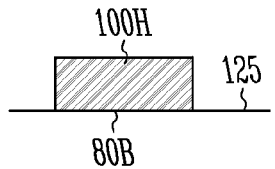
Figure 8C:
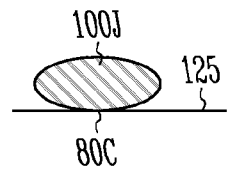

FIGS. 8A, 8B and 8C illustrate sectional views of a segment of support structures 100G, 100H and 100J, respectively. In FIG. 8A, support structure 100G has a circular or round section and bears on tissue 125 at contact surface 80A. In FIG. 8B, support structure 100H has a rectangular section and bears on tissue 125 at contact surface 80B. In FIG. 8C, support structure 100J has a semi-circular section and bears on tissue 125 at contact surface 80C. The shape and size of contact surfaces 80A, 80B and 80C are selected to provide a desired surface area of contact with tissue 125. In various examples, support structure 100 is formed of wire or sheet stock. In other examples, support structure 100 is formed by rolling, etching, stamping, machining, casting, or by other fabrication means. In one example, the support structure is placed in position using a cannula having an interior profile that matches that of a section of the support structure.

Support structure 100 can be formed of solid, hollow (or tubular), laminated or built-up structures including any of a variety of metals or non-metals. Exemplary materials for support structure 100 include stainless steel, nitinol or other shape memory or superelastic material, and a polymer or biodegradable polymer. Support structure 100 can include elastic or non-elastic materials. In one example, support structure 100 is non-magnetic.

In one example, the present subject matter includes a ring fabricated of a shape memory material and the ring is inserted through a tube through the pars plana region of the eye. Following insertion, body heat raises the temperature of the ring and causes the ring to transition from a first configuration or shape to a second configuration or shape. In one example, the superelastic properties of the support structure allow it to be deformed significantly as it is introduced into the eye and return to its original shape once inside the eye.

Figure 9:
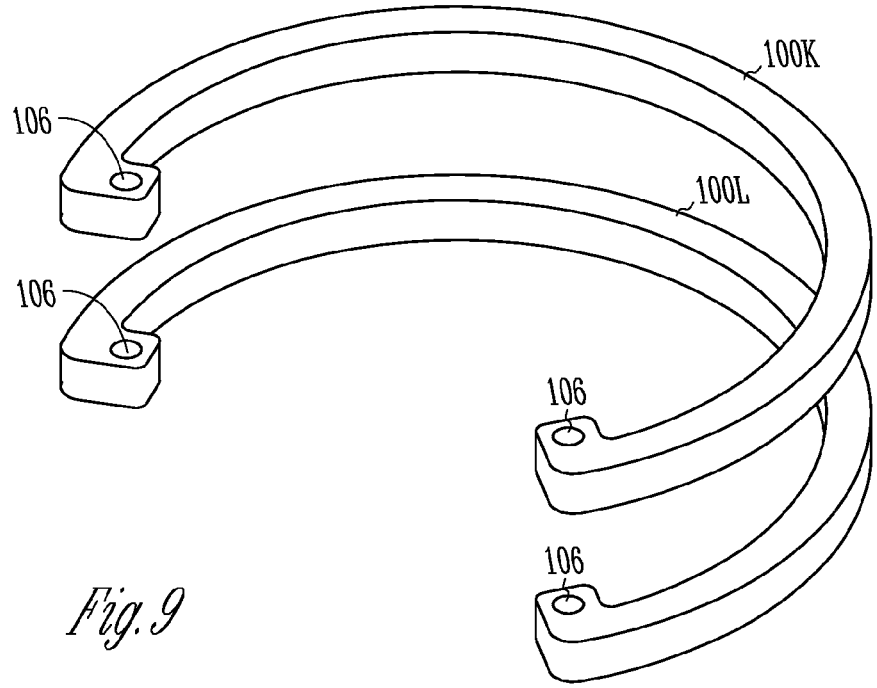
FIG. 9 illustrates a perspective view of a support structure.

FIG. 9 illustrates an exemplary support structure formed of separate semi-circular rings denoted as rings 100K and 100L. In the figure, rings 100K and 100L have approximately matching overall diameters and are fabricated of wire. The wire can be wound or rolled. Features located at the ends of ring 100K and ring 100L include holes 106. Holes 106 can be blind holes, divots, dimples or through holes. In the example illustrated, holes 106 provide electrical contact with rings 100K and 100L. In one example, holes 106 are configured to receive a surgical tool that may help manipulate rings 100K and 100L.

In one example, ring 100K serves as an electrical supply electrode and ring 100L serves as an electrical drain electrode. A current passing between the supply and drain electrodes serves to activate the support structure and thus bond to the tissue.

As illustrated, rings 100K and 100L present a relatively small footprint. The surface area in contact with the tissue is small relative to the surface area of the tissue supported by the support structure.

Figure 10:
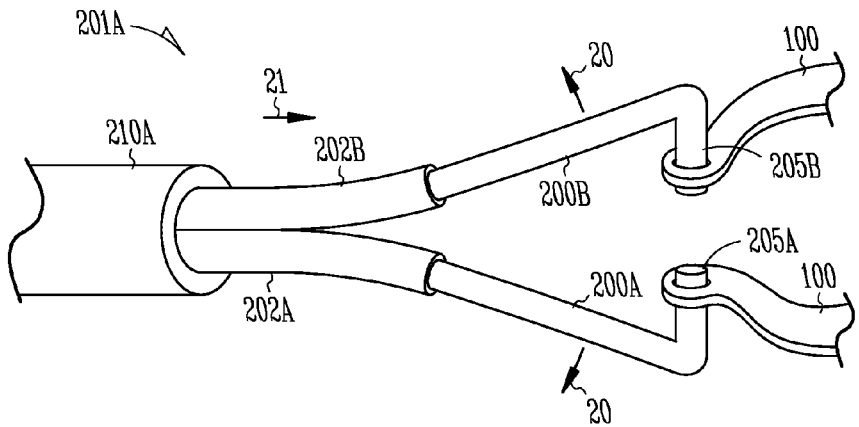
FIG. 10 illustrates a tool.
Figure 13:
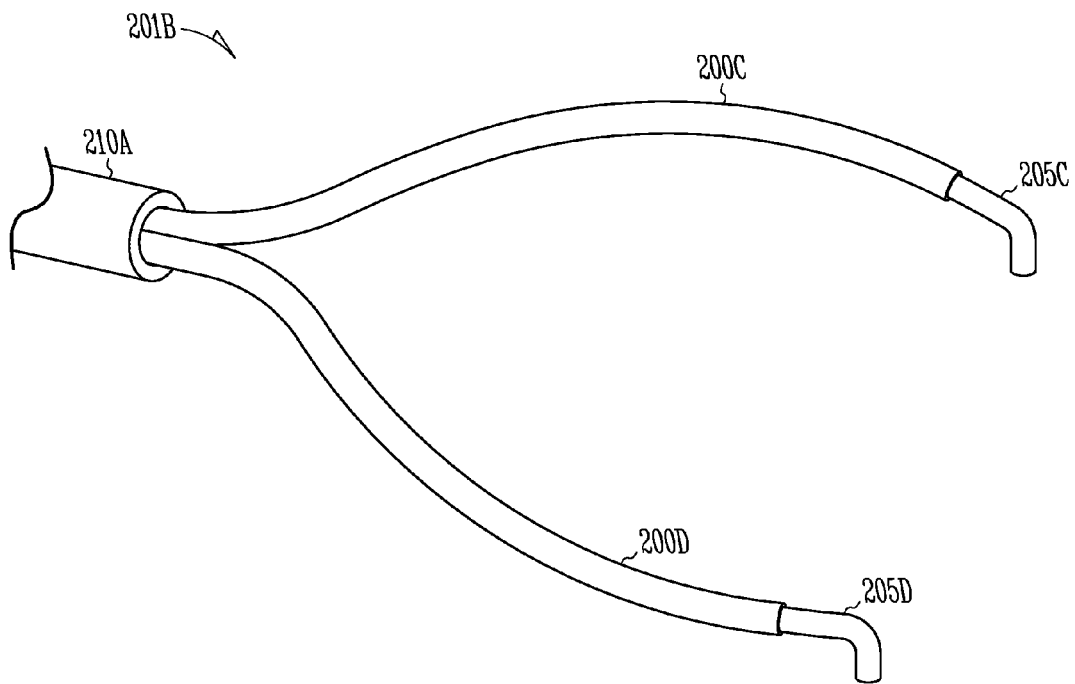
FIG. 13 illustrates a tool.

FIGS. 10 and 13 illustrate tools 201A and 201B, respectively, with tool 201B particularly suited for manipulating, placing and activating the structure illustrated in FIG. 9. In one example, the tool is used for capturing the graft and for insertion of the graft into the destination.

In FIG. 10, tool 201A includes formed linear members 200A and 200B having ends 205A and 205B, respectively. Linear members 200A and 200B are disposed in a lumen of cannulas 202A and 202B, respectively. Cannulas 202A and 202B are disposed within a lumen of guide 210A and an opposite end (not shown) provides access for manipulating, placing and activating a structure coupled to ends 205A and 205B. In one example, ends 205A and 205B of tool 201A are shaped in a manner that presents opposing convergent faces to facilitate coupling with a structure, such as that illustrated in FIG. 9. In one example, ends 205A and 205B are shaped in a manner that forms opposing divergent faces. Other configurations for ends 205A and 205B are contemplated. Linear members 200A and 200B are formed of electrically conductive or non-conductive materials and can be laminated, coated, solid or hollow. Linear members 200A and 200B can be manipulated together or independent of each other.

In various examples, tool 201A is used to insert, place or position exemplary support structure 100 shown partially in the figure. In one example, tool 201A is used to deliver energy to bond support structure 100 to tissue. In the figure, ends 205A and 205B are shaped to enter holes of support structure 100 from opposite sides, however, in other examples, the ends enter holes or other features of support structure 100 from a single side. Ends 205A and 205B are urged apart by a resilient force operating in the direction shown at arrows 20. Ends 205A and 205B can be drawn together by relative movement of guide 210A in the direction shown by arrows 21, or movement of cannulas 202A and 202B relative to guide 210A. In one example, cannulas 202A and 202B are configured for independent movement relative to each other as well as independent movement relative to guide 210A.

FIG. 13 illustrates tool 201B having curved linear members 200C and 200D in the positions shown. These members may be retracted into a straight configuration for insertion through a small incision. A portion of the length of linear members 200C and 200D is coated with a dielectric (such as polyimide). Bare ends 205C and 205D provide electrical connection to support structure 100. For example, ends 205C and 205D can be manipulated to connect with features of a structure, including, for example, selected holes 106 of rings 100K and 100L. Guide 210A provides an insulative sheath by which linear members 200C and 200D can be manipulated. In one example, the support structure is manipulated based on relative motion between the guide 210A and the linear members.

Ends 205C and 205D are shaped to engage a support structure for purposes of manipulating and activating the support structure. In the example illustrated, ends 205C and 205D include elbow portions that allow insertion into receiving holes of a support structure from one side of the support structure. Other configurations for the ends are also contemplated. Ends 205C and 205D, as illustrated, facilitate delivery of electrical energy to an exemplary support structure.

Figure 11:
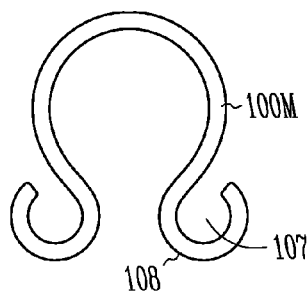
FIG. 11 illustrates a view of a support structure.

FIG. 11 illustrates support structure 100M having a circular configuration with loop feature 107 disposed at end 108. In one example, loop feature 107 includes a formed wire loop configured to engage with a device such as tool 201A or tool 201B.

Figure 12A:
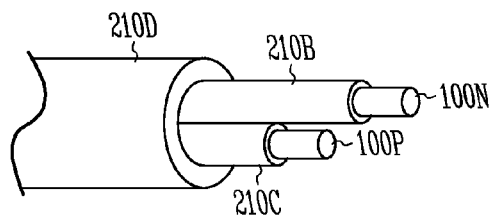
FIGS. 12A, 12B and 12C illustrate support structures in various configurations.
Figure 12B:
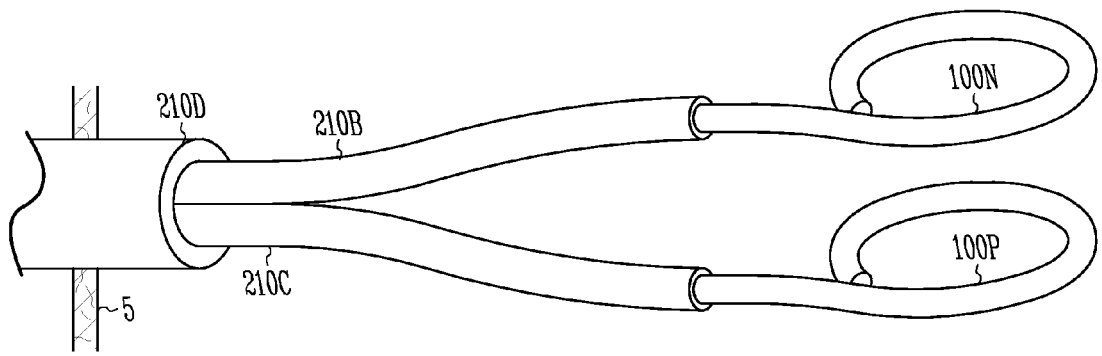
Figure 12C:
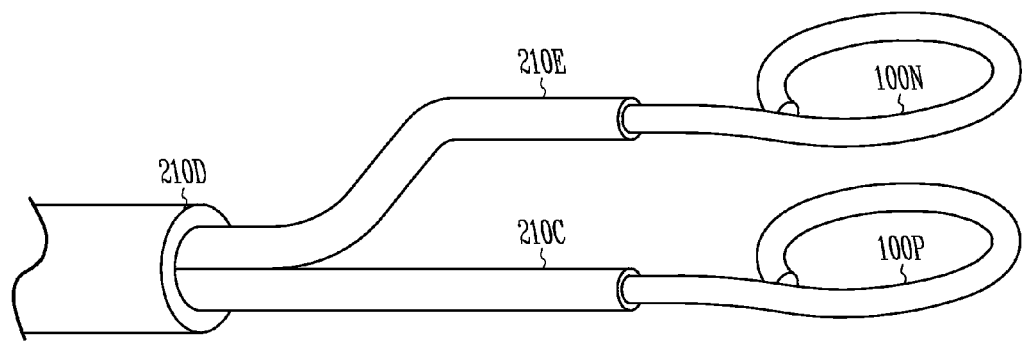

FIG. 12A illustrates an embodiment of a support structure in a retracted position and FIGS. 12B and 12C illustrate alternative examples of the structure in a deployed configuration. In FIG. 12A, insulative sheath 210D (also referred to as a cannula) and guides 210B and 210C (also referred to as a cannula) constrain the deflection of ring 100N and ring 100P where ring 100N and ring 100P are illustrated in an uncoiled configuration. In one example, guides 210B and 210C have a common sheath with a rotational component for manipulation of ring 100N and ring 100P either simultaneously or independently. In various examples, rings 100N and 100P are fabricated of elastic or shape memory material. For example, rings 100N and 100P can be distorted to a substantially linear configuration, as shown in FIG. 12A and later return to a formed configuration when external constraints or forces are removed (as with an elastic material) or upon transition from a first temperature to a second temperature (as with a shape memory material). In one example, an intraocular infusion fluid (cooling or heating) can be used to trigger a transition of a shape memory material from a first configuration to a second configuration, in addition to controlling an intraocular temperature.

The cannula can have two lumens (as shown in the figures) or more than two lumens. In addition, the multiple lumens of the cannula can each carry a pushrod for deployment, manipulation, or activation of a support structure.

In one example as illustrated in FIG. 12A, each of insulative sheath 210D, guide 210B, guide 210C, ring 100N, and ring 100P are configured for independent movement relative to each other. For instance, guide 210B can be manipulated independently relative to sheath 210D as well as ring 100N, ring 100P and guide 210C.

In FIG. 12B, linear members 210B and 210C are configured in a curved or swept formation with each linear member deflecting a similar amount from a center line upon relaxation. FIG. 12B illustrates a sectional view of insulative sheath 210D penetrating a tissue wall 5. In FIG. 12C, linear member 210E is configured in an angular formation and linear member 210C is configured in an unbent formation with linear member 210E deflecting away from linear member 210C. For the example illustrated, linear member 210E has a length that exceeds linear member 210C when in a retracted position. Linear member 210E is configured with two hinge points or knees, however, in other examples, one or more of the linear members are shaped with more or less curvature.

Figure 12D:
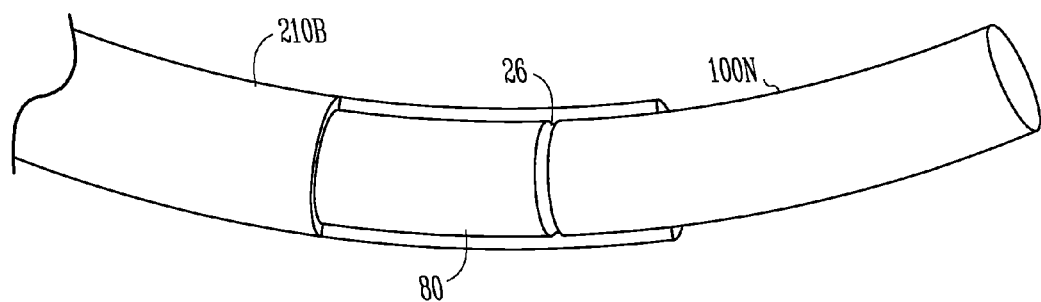
FIG. 12D illustrates a cut-away view of a support structure partially disposed in a cannula.

FIG. 12D illustrates a portion of a support structure having ring 100N disposed partially within a lumen of cannula 210B. Ring 100N is shown in an uncoiled configuration. In one example, ring 100N includes a shape memory material. Ring 100N is ejected by a force applied to pushrod 80, also disposed within a lumen of cannula 210B. In the figure, both of ring 100N and cannula 210B have a curvature that facilitates placement (and extraction) of the support structure. In other examples, either one or the other of ring 100N and cannula 210B has a curvature. In one example, the structure is naturally coiled and when restrained by the confines of the lumen, maintains a substantially linear configuration but when ejected from within the lumen, it assumes a ring shape or other configuration. Break 26 depicts the separate nature of pushrod 80 and ring 100N. In one example, break 26 includes a keyed joint, such as a tongue and groove, screw, or a spline, to allow rotational control of the support structure from the distal end of the pushrod. Break 26, in one example, includes a weakened portion where pushrod 80 can be physically separated from ring 100N by applying a force. The curved cannula, when disposed through the sclera, may reduce strain on the tissue wall of the eye and support structure during introduction into the eye.

In one example, ring 100N is naturally coiled and when restrained by the confines of the lumen, maintains a substantially linear configuration but when ejected from within the lumen, it assumes a ring configuration. Break 26 depicts the separate nature of pushrod 80 and ring 100N.

Rings 100N and 100P, for example can be separate from a pushrod or can be contiguous segments that are clipped or configured to break at a predetermined location, thus separating from the pushrod or other member that remains in the lumen.

A suitable shape memory material is selected to have a transition temperature based on the body temperatures encountered in the eye. For example, the support structure material is selected to retain a first shape or configuration at a first temperature (which can be greater than or less than that of the eye) and then resort to a second shape or configuration upon exposure to a second temperature different from the first temperature. In one example, the material has elastic or superelastic properties.

Shape memory materials (or metals) have a thermal memory. Nitinol is an example of a shape-memory alloy and its shape-memory effect is due to a reversible austenite-martensite transformation. In the low-temperature regime, the alloy exists as a complex arrangement of atoms called martensite. As the alloy is heated through a transition temperature range, the alloy undergoes a solid-to-solid phase change to the highly ordered parent phase, called austenite. It is possible to control the transition temperature range by changing the nickel-titanium ratio, or by alloying with other metals. In one example, the nitinol structure that is introduced into the body has a transition temperature near body temperature. A nitinol structure can be cooled and compressed for delivery, and when deployed, it warms to body temperature, and returns to the parent shape.

To impart a parent shape to a nitinol structure, it must be constrained in the desired, final shape and heated in a furnace to between approximately 450 and 550 degrees C. This produces an austenitic structure. The part can then be cooled and compressed or deformed to produce a martensitic structure. Subsequent heating beyond the transition temperature allows the structure to return to its memory position.

Ni—Ti is an example of a shape memory material with superelastic properties used in biomedical applications. Other alloys that exhibit shape memory properties include Cu—Al—Ni (copper-aluminum-nickel), Cu—Zn—Al (copper-zinc-aluminum), Au—Cd (gold-cadmium), and Ni—Al (nickel-aluminum). Some shape memory alloys also exhibit superelastic behavior. Examples of superelastic alloys include Cu—Al—Ni (copper-aluminum-nickel), Cu—Al—Mn (copper-aluminum-manganese), In—Pb (indium-lead), and Cu—Al—Be (copper-aluminum-beryllium). Non-metallic materials are also contemplated for shape memory materials and superelastic materials.

A structure having a first shape (first configuration) can be deformed to allow passage through an opening or cannula through the sclera. Accordingly, to pass through the eye, the structure is deformed or partially uncoiled into a second configuration. After passing into the eye, the constraining force exerted by, for example, the cannula, is removed and the structure returns to the first configuration. Nitinol can sustain a strain below approximately 8% and exhibit the superelasticity property as described herein.

Figures 14A, 14B, 14C:
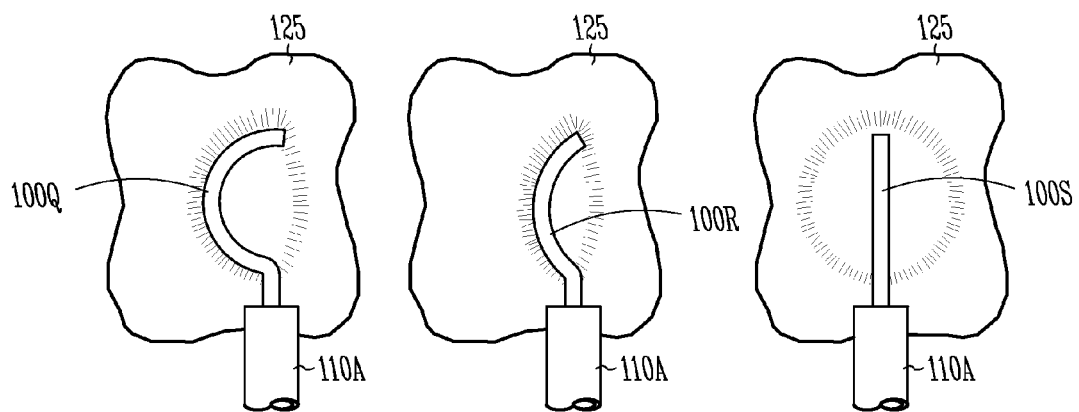
FIGS. 14A, 14B and 14C illustrate exemplary support structures and corresponding coagulated regions.

FIGS. 14A, 14B and 14C illustrate exemplary support structures having a variety of configurations. Support structures 100Q, 100R, and 100S are shown having a hemicircular (half), semi-circular (partial), and unbent configuration, respectively. In each figure, a region of tissue 125 is illustrated underlying each support structure. Each support structure 100Q, 100R and 100S is disposed in guide 110A. In various examples, a corresponding portion of a support structure (not illustrated) is disposed underneath tissue 125. The corresponding portion can have a similar or different size or configuration as the upper portion.

The tissue is cauterized in the regions illustrated by the radial lines underlying the support structures. In one example, the support structure is illustrated as a straight segment. In one example, the support structure includes a split or forked element that deploys to a "V" shaped segment in which case the perimeter of the "V" is cauterized and cut. Other geometric configurations and sizes for support structures are also contemplated.

Figure 15A:
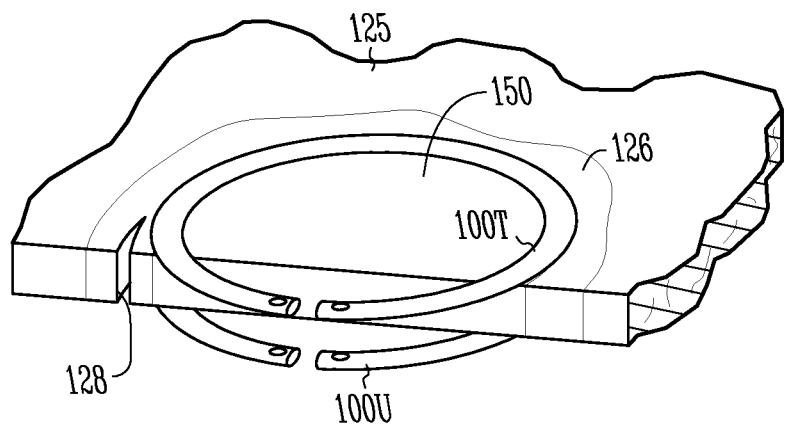
FIGS. 15A and 15B illustrate perspective views of exemplary support structures and a portion of tissue.

FIG. 15A illustrates a perspective view of a support structure having ring 100T and ring 100U positioned on opposite surfaces of a section of tissue 125. In the figure, both ring 100T and ring 100U are illustrated in the form of split circular rings of a similar size. Coagulated region 126 encircles a periphery of the support structure and penetrates through the entire depth of tissue 125. Cut 128 is disposed within coagulated region 126 and encircles a portion of the periphery of ring 100T. The subject matter of FIG. 15A is configured to form a free graft for translocation.

The split portions in rings 100T and 100U are illustrated near an edge of the tissue. Other locations or alignments of the splits are also contemplated. The figure also illustrates holes disposed at the ends on either side of the splits. In one example, the holes facilitate manipulation and activation of the support structure.

A method according to the present subject matter includes placing the support structure about a target location on at least one surface of the tissue. In FIG. 15A, target 150 is encircled by both ring 100T and ring 100U. After placement of the support structure and activation to bond the structure to the tissue (including ring 100T and ring 100U for the example illustrated), coagulated region 126 is formed on a surface of tissue 125 around the periphery of the support structure. Cut 128 is formed within the coagulated region followed by removal or separation of target 150 from tissue 125. Target 150 is then translocated to a destination location and affixed in position. In various examples, ring 100T and ring 100U provide a support structure by which target 150 is manipulated and positioned. In the example illustrated in FIG. 15A, target 150 is completely separated from tissue 125 by coagulating and cutting around the entire periphery.

Figure 15B:
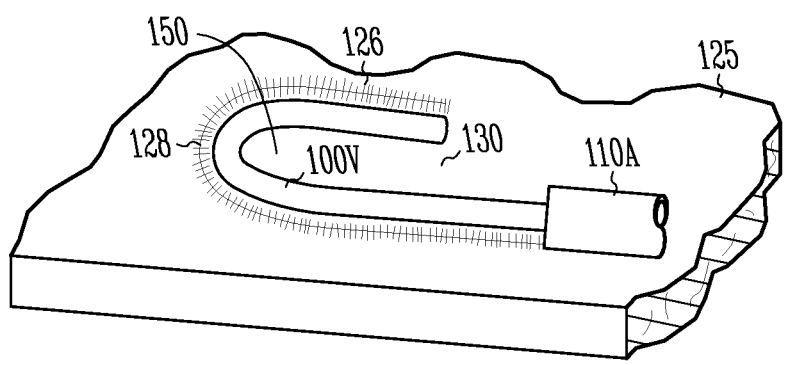

In one example, the target tissue is partially separated from tissue 125 and a portion of the tissue and target remain contiguous. FIG. 15B illustrates such an example with support structure 100V disposed on an upper surface of tissue 125. In one example, a second portion of the support structure (not illustrated) is provided on a lower surface of tissue 125. Coagulated region 126 is formed around a portion of support structure 100V and cut 128 is formed therein. Target 150 is located proximate a portion of support structure 100V and remains attached to tissue 125 at region 130. Region 130 is distorted when target 150 is rotated, or relocated, to a destination location by manipulating support structure 100V and guide 11 OA. The subject matter illustrated in FIG. 15B allows formation and translocation of a pedicle graft where the target remains attached to the tissue and blood perfusion to the graft continues. In one example, the cauterized region, and the incision are located very close to the perimeter of the support structure.

Figure 16:
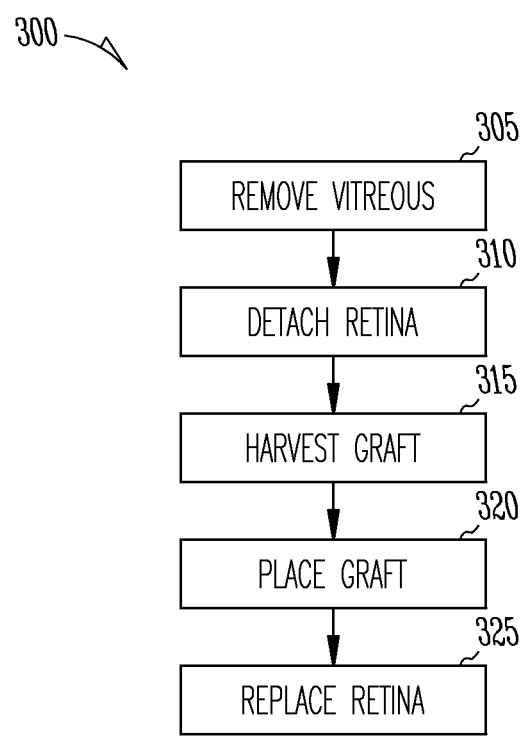
FIGS. 16 and 17 illustrate exemplary methods of the present subject matter.

FIG. 16 illustrates a flow chart of method 300 according to the present subject matter. At 305, a standard 3-port pars plana vitrectomy is performed, removing the core vitreous, lifting the posterior vitreous from the retinal surface, and removing the majority of the posterior vitreous gel. At 310, the retina is detached. At 315, the graft is harvested. At 320, the graft is placed in position at the destination. At 325, the retina is replaced.

Figure 17:
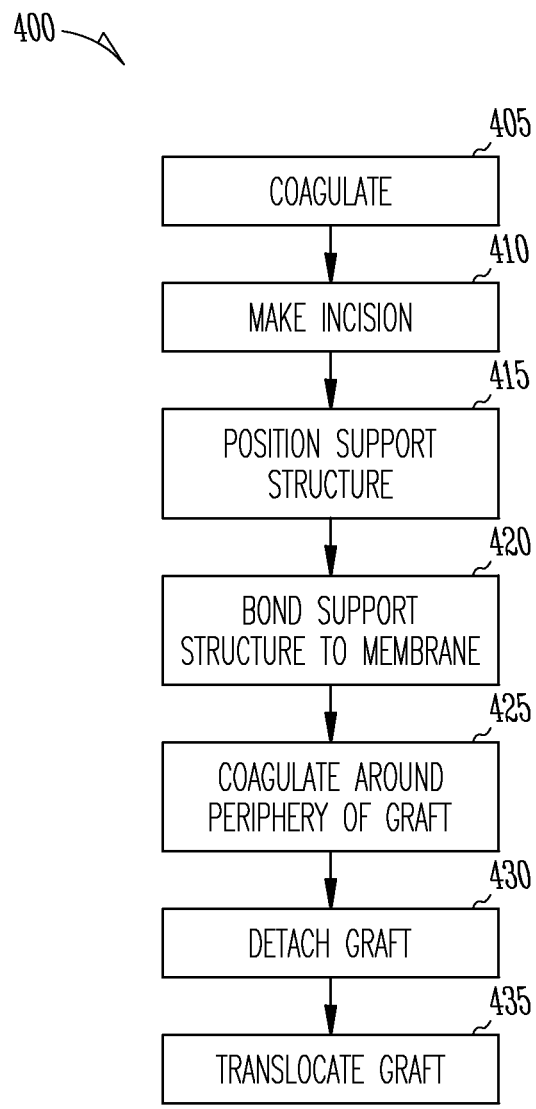

FIG. 17 illustrates a flow chart of method 400 according to the present subject matter. At 405, tissue is coagulated in order to reduce bleeding. At 410, an incision is made to gain access to the suprachoroidal space. At 415, support structure 100 is positioned proximate target 150 on tissue 125. At 420, support structure 100 is bonded to tissue 125 or other membrane. At 425, tissue 125 around support structure 100 is coagulated. At 430, graft or target 150 is detached from the surrounding tissue 125. At 435, graft 150 is relocated to the macular region, thereby supporting the neurosensory retina with a translocated autograft of healthy choroid, Bruch's membrane, and RPE.

In one example, the retina is left intact. The full-thickness retina, RPE, Bruch's membrane, and choroid are coagulated using a thermal modality, such as pulsed laser. Next, an incision is made along the nerve fiber layers of the retina. The posterior ring of a support structure is placed in the suprachoroidal space between the choroid and the sclera. The anterior ring, aligned with the posterior ring, is placed upon the innermost layer of the neurosensory retina. The rings are activated, and the graft, (including choroid, Bruch's membrane, RPE, and neurosensory retina), is removed. The neurosensory retina is then gently peeled away from the graft, leaving a layer of choroid, Bruch's membrane, and RPE supported by the structure. The graft is then inserted as described.

In one example, the support structure is placed and positioned without detaching the superior retina at a localized position. In such a procedure, a small blister, or induction of a serous retinal detachment, is made and an incision is made in the nerve fiber layers in a direction parallel to the grain of the fibers. In one example, the support structure is inserted under the separated nerve fiber layer.

In one example, the translocation procedure includes removing the damaged tissue underlying the retina. In one example, the damaged tissue remains in place and the translocated patch of choroid, Bruch's membrane, and RPE is placed beneath the retina in a position on top of the original damaged tissue. Over time, new vessels grow through the original tissue to perfuse the new graft. The removal of the damaged tissue underlying the macula is optional.

Figure 18:
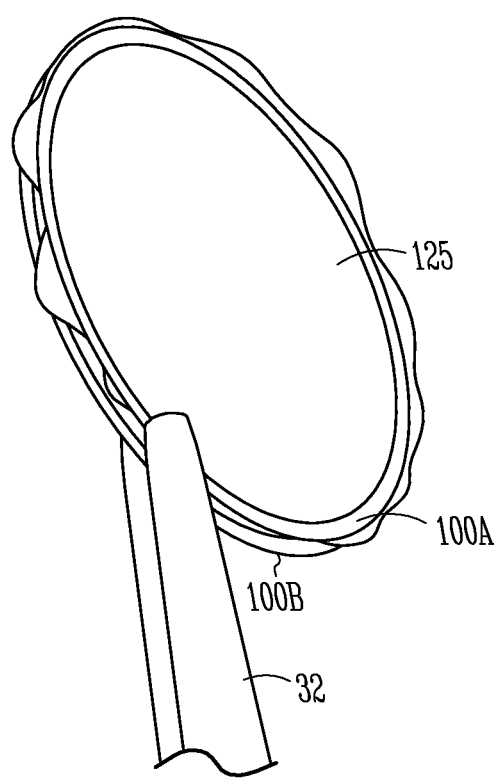
FIG. 18 illustrates a perspective view of a graft supported by an exemplary support structure.

FIG. 18 illustrates a view of an excised autologous graft of choroid, Bruch's membrane, and RPE supported by a support structure including two nitinol rings. Tissue 125 is held in a position that reveals the RPE with underlying layers not visible. Anterior ring 100A is largely visible and portions of posterior ring 100B are visible only where the cauterized tissue is cut closer to the rings. Prior to harvest of the graft, posterior ring 100B is positioned between the sclera and the choroid. Forceps 32 is shown gripping ring 100A and 100B.

Alternate Examples

In one example, tissue other than choroid, Bruch's membrane, and RPE is manipulated and translocated using the present subject matter. For example, other vascular tissue includes the choroid plexus in the central nervous system, vascular complexes in the gastrointestinal system including the small bowel, colon and stomach tissue, vascular plexus of the bladder or urinary tract system, pericardium with its inherent microvasculature, meninges surrounding the central nervous system, vascular plexus surrounding nerve tissue, subcutaneous vascular tissue (subdermal), vascular complexes in the sinuses or oral mucosa, nasal pharynx or esophagus.

In one example, fluid is introduced under the retina into the subretinal space to aid in detachment of the retina.

The present subject matter is configured to facilitate transplantation of healthy RPE with a full-thickness patch of underlying Bruch's membrane and choroid. The present subject matter can be used to harvest and translocate a patch of tissue while maintaining the shape, size, and polarity of the patch or graft. In one example, an autologous graft of choroid, Bruch's membrane, and RPE is moved to the subfoveal area and placed beneath the macula.

It is expected that new blood vessels may form to provide choroidal blood flow to support the RPE.

The present subject matter may eliminate the problem of torsional diplopia, a tilted horizon in the surgical eye that sometimes results from macular translocation surgery. A temporary, surgical retinal detachment provides access for the surgery. The retina is reattached in its original position and maintains normal orientation.

In one example, a flap (shaped like a peninsula) of healthy choroid, Bruch's membrane, and RPE is repositioned by rotation of the flap under the retina to replace a region of damaged choroid, Bruch's membrane, and RPE that is no longer capable of supporting the photoreceptors in the retina. The flap, or pedicle, remains connected to the choroidal blood supply to nourish the flap tissue.

In one example, a free, autologous graft of healthy choroid, Bruch's membrane, and RPE is harvested from the patient's eye and repositioned under the macula. The neovascularization from the choroid will vascularize the graft.

In one example, an allograft (tissue transplanted from a donor to a recipient) is performed using the present subject matter. As such, the host is subjected to immunosuppression since the graft would be treated as foreign tissue by the recipient's immune system. In one example, the graft can be obtained from a cadaveric source such as an eye bank. In one example, tissue from the fellow eye is used as an autograft, thereby avoiding immune barriers. As such, tissue (including choroid, Bruch's membrane, and RPE) from one eye is translocated to the macular region of the fellow eye of the donor.

In one example, a patch includes a synthetic graft. A synthetic graft can be grown in vitro, from, for example, donor stem cells, iris cells, or other sources.

In one example, a layer of photoreceptor cells is implanted on a support structure as described herein and used to replace cellular elements lost in other retinal degenerative conditions such as retinitis pigmentosa.

Coagulation around the patch can damage the RPE. Additionally, Bruch's membrane has a tendency to shrink when exposed to energy that is capable of coagulating choroidal blood vessels. In one example, the shape and orientation of the graft is maintained by the support structure while repositioning the graft, thus reducing the amount of tissue damaged during the process. An index mark or a feature position can be used as a reference to maintain alignment of the graft orientation. The index mark or feature can be disposed on one or more portions of the support structure.

In one example, a micro-pulsed diode laser is used to coagulate the periphery of the patch. The laser is operated with particular parameters as to maximum power, length of pulse and length of interval between pulses.

Typical radio frequency (RF) generators for intraocular devices have a maximum power in the range of 12-15 W. In one example, the support structure is bonded to the tissue using a power level ranging from about 1 W to 10 W. Parameters for bonding the tissue to the support structure, including power level, pulse duration, and frequency can be established experimentally.

In one example, a foot pedal is used to apply power to the electrodes momentarily. In one example, the device is operated briefly to tack the support structure into position at one or more locations around the periphery. Typically, during the bonding process, some regions of tissue stick to the electrodes, thus forming a thin layer of insulation. To overcome the thin layer of insulation, the power is slightly increased in order to maintain the same activation or bonding effect. If excessive tissue sticks to the electrodes, increased power levels have little effect and the electrodes can be cleaned to restore bonding effectiveness.

In one example, the support structure includes an implantable structure of biocompatible metal to support the graft during harvest and facilitates repositioning of the graft. In various examples, the support structure is in the form of a ring or other structure having an approximately circular shape.

In one example, the support structure is fabricated of a shape memory material such as nitinol (a nickel titanium alloy originally developed at the Naval Ordnance Laboratory). Nitinol has shape-memory characteristics that allow it to be folded into a compact shape for insertion through a small tube (for example, a 20 gauge blunt needle) inserted into the eye, and then deployed (by exposure to body temperature) to return to its memory position for use as a support structure.

In one example, the support structure is inserted or retracted using a guide of 18 gauge (approximately 1.02 mm diameter); however, larger or smaller diameters are also contemplated. Entry sites through the sclera (sclerotomy) may range from 25 gauge to 18 gauge or larger.

In one example, the support structure is bonded to the graft and provides a structure with which to manipulate and position the graft, or patch. In one example, the orientation and polarity of the RPE cells remain aligned with that of the surrounding tissue.

In one example, the support structure includes two rings, one on top of the RPE and one beneath the choroid and each serves as an electrode for applying pulsed radio frequency (RF) energy. The two rings bond to the tissue and provide support for the graft.

Various bipolar devices can be used to activate the support structure. In one example, a bipolar device and a signal generator are used for delivering RF energy to the support structure. For example, a bipolar scissors can be used for cutting and coagulation. In one example, an intraocular (bipolar) forceps is adapted to activate the support structure. In various examples, the support structure includes members disposed on one or two surfaces of the graft. In addition to bipolar devices, the support structure can also be bonded using a monopolar device. In a monopolar device, RF current flows in the tissue between a small active electrode and a passive, neutral or dispersive electrode which has a much larger surface area. In a bipolar device, RF current flows in the tissue between two closely spaced electrodes.

In one example, laser ablation and cutting (for example, with a diamond knife) are used around the outer periphery of the support structure of the choroid, Bruch's membrane, and RPE tissue. In one example, the upper and lower (or first and second) rings of a support structure are clamped in concentric alignment to elevate and separate tissue, protect the RPE cellular layer or other delicate monocellular layers that are being translocated, and to separate tissue on either side of the choroid, Bruch's membrane, and RPE.

In one example, air (in the form of bubbles), or fluid (such as balanced salt solution, perfluorocarbon liquid, hyaluronate, or other viscoelastic agent) is introduced to elevate and separate tissue to allow placement of the graft in the subretinal space or other destination for target 150. The bubbles, fluids, or liquids can also be used in the insertion site to protect delicate cellular layers, and prevent injury. Accordingly, the graft is positioned between the existing RPE and the neurosensory retina (photoreceptors) in the macular region. The graft is centered to support the fovea. In one example, the fovea of the neurosensory retina is positioned to lie at the center of target 150.

In one example, a laser is used to cauterize tissue around the graft.

In one example, the support structure is fabricated of biodegradable material and thus, breaks down after a predetermined period following translocation of the graft.

In one example, the support structure is encased in a naturally occurring fibrous capsule and remains in position following translocation of the graft.

In various examples, the support structure includes a feature, such as a tab, that facilitates manipulation and positioning of the graft.

In various examples, the support structure is used to cauterize the tissue around the graft. For example, electrically conductive rings can serve as cauterizing electrodes and the rings are placed and positioned using forceps or another tool having electrically charged contacts. In one example, the tool includes a vertically acting forceps. In one example, the tool is manipulated through a guide having a diameter of approximately 2 mm. In various examples, the forceps are used to insert the support structure through a guide as well as to grasp, position, and activate the support structure.

In one example, access to the graft is provided (for either retrieval or insertion) through the sclera by creating a larger scleral opening externally with standard blades and addressing the choroid with laser, diathermy, or cautery.

In one example, the support structure includes two members that are positioned with one on either surface of the tissue. In various examples, the two members are aligned by manual alignment, a hinge, a pivoting bracket or aligned by a placement structure as illustrated herein. In one example, the members of the support structure are aligned by visually noting deflection telegraphed through from an opposite side of the tissue.

In one example, a layer of oxide is removed from a metal support structure to facilitate bonding to the tissue.

In various examples, the surface of the support structure is modified to enhance bonding. Exemplary modifications include roughening, scoring, serrations, or ridges on the surface of the support structure.

In various examples, the support structure is positioned by means of a linear incision or a pierced hole. The support structure can be distorted or collapsed into a first configuration and inserted into position and thereafter deployed or allowed to revert to a second configuration.

In various examples, the support structure is affixed in position by an activation process that produces a change in collagen as energy is delivered, thus causing the tissue to adhere to the support structure. Activation can include application of thermal energy (freezing or heating current), RF energy, electric current or optical energy. In one example, a radio frequency (RF) bipolar generator is used to activate the support structure and form a bond with the tissue. In one example, a biocompatible adhesive is used to bond the support structure to the tissue.

In various examples, a laser light source is directed around the periphery of the support structure to coagulate the blood around the graft. In one example, low level pulsed energy is applied to avoid shriveling, shrinkage and tissue damage. In one example, the power level is approximately 750 milliwatts and the pulse interval is reduced to deliver sufficient energy per unit time in order to coagulate. At low energy levels, the line can be traced repeatedly in order to produce an acceptable burn.

The absorption rate also depends on the level of pigmentation in the eye. For example, in micropulse mode with an 810 nm diode laser, a power of approximately 850 mW, a pulse duration of 100 microseconds, and a pulse interval of 500 microseconds can produce effective results. Other power levels, durations and intervals are also contemplated. In one example, the power level may be in the range of 500 mW to 2000 mW depending on the level of pigmentation and other factors.

In one example, a tab or other feature is provided on a support structure and energy is coupled to the support structure by the feature.

In one example, the laser energy is directed at the tissue and measures are taken to avoid absorption by the support structure. For example, a coating or sacrificial structure (such as an additional wire ring) is provided to reduce losses at the support structure.

The laser energy is directed around the support structure by manual manipulation of a tool or by indexing off the support structure. In one example, the support structure includes a side-emitting optical fiber element and optical energy pulsed in the fiber serves to ablate or coagulate the tissue around the graft.

In various examples, the support structure is treated with a pro-vascular or an anti-vascular drug to modulate perfusion of the graft following translocation. In one example, the drug is incorporated as a drug eluting coating on the support structure. In one example, a scleral depressor is used to place the support structure in position. For example, an external thrust device can be used to apply a pressure to a portion of the sclera to facilitate identification of the target site. The blood vessels will appear blanched and thus provide a guide as to cauterizing.

In one example, choroidal blood vessels are blanched to facilitate coagulation. Blanching can reduce the thermal spread of vascular blood flow to surrounding tissues (radiator effect) and thus also allow closure of vessels without actively flowing blood.

In addition, blanching before coagulating may allow the laser energy level to be lower. The tissue may coagulate with reduced thermal damage if tamponade is provided by, for example, an external scleral depression device, sufficient to blanch the choroidal tissue. Application of visible light (illumination) in conjunction with scleral depression can facilitate identification of the blanched tissue.

In one example, selected drugs or factors are used with the support structure to enhance engraftment. Exemplary anti-angiogenesis drugs include Lucentis™ (ranibizumab, a humanized anti-VEGF antibody fragment that inhibits activity) or MACUGEN® (pegaptanib sodium injection) and exemplary pro-angiogenic peptides such as VEGF. In various examples, a first drug or surface treatment is used on a first member of a support structure and a different or second drug or surface treatment is used on a second member of the support structure.

In one example, a balloon depressor or other structure to depress the sclera is used to compress a target area. After depressing the target area, a laser is used to coagulate the surrounding tissue. After removing the depressor (or deflating the balloon), the support structure is introduced and placed in position on one or both sides of the tissue. The graft is then excised by cutting followed by translocation and re-implantation. In one example, a scleral depressor is used to tamponade the choroidal blood flow to improve coagulation.

The depressor can facilitate blanching of the blood vessels. The tissue blanches, or turns a pale color when pressure is applied.

In one example, pre-existing tissue is removed from the destination site prior to translocation and re-implantation. In one example, the graft is translocated and re-implanted without removal of pre-existing tissue.

In one example, the support structure members (or portions) are disposed on the first and second surface of the tissue and are spaced apart by a distance of approximately 400-500 microns. In various examples, the support structure members are spaced apart by a dimension less than 400 microns and in other examples, by a dimension greater than 500 microns. The support structure members are separated to reduce or eliminate damage to the tissue, particularly the RPE, by scraping. In one example, a portion of the support structure is coated with a material selected to protect the RPE, such as a viscoelastic substance, and thereby reduce loss of RPE.

In various examples, the tissue is coagulated on either one or both surfaces. In one example, an incision is formed on either one or both surfaces. In one example, the support structure is affixed to one surface of the tissue and an opposite surface of the tissue is coagulated. In one example, the support structure is affixed to one surface of the tissue and an opposite surface of the tissue is cut. The tissue is cut with a scissors, a laser, a diamond blade, or other cutting tool.

FIGS. 19A and 19B illustrate sectional views of portions of a support structure. In FIG. 19A, support structure 190A includes ring 192A and ring 194A. Ring 192A has a substantially rectangular cross section with groove 191 disposed on the tissue contact surface. Ring 194A has a substantially rectangular cross section with tongue 193 disposed on the tissue contact surface. Tongue 193 and groove 191 are configured to match and facilitate alignment of ring 192A and ring 194A disposed on opposite sides of the membrane (not shown).

In one example, the two rings of a support structure are aligned by a series of raised dimples or spikes on one ring and a corresponding series of depressions or holes on the second ring. The combination of protruding portions and receiving portions may facilitate holding the support structure in position relative to the tissue.

In FIG. 19B, support structure 190B includes ring 192B and ring 194B. Ring 192B and ring 194B have sections corresponding to partially flattened round stock. The round stock can be flattened by rolling. Ring 192B and ring 194B are held in alignment by hinge 195. Hinge 195, in various examples, includes a flexible element or mechanical structure that allows limited movement of ring 192B relative to ring 194B. In one example, hinge 195 includes a shape memory material.

FIGS. 20A, 20B and 20C illustrate exemplary features for manipulating the support structure. In FIG. 20A, for example, support structure 250A is affixed to feature 260. Feature 260 includes a ball-like structure that is configured for grasping by a manipulator having a corresponding cup-shaped element. In FIG. 20B, for example, support structure 250B includes feature 262 disposed on a surface. Feature 262, in the figure, includes a hole or cavity that receives a manipulator having a corresponding element. In one example, the hole includes a "t-slot" or other shaped element that allows an operator to manipulate, control and engage the support structure. In FIG. 20C, for example, a resilient portion of manipulator 276 engages a corresponding feature of support structure 250C. In the figure, manipulator 276 includes ramped portions 272 that engage hole 261 in the support structure 250C. Notch 274 of manipulator 276 engages the surfaces of hole 261 of support structure 250C following deflection of ramped portions 272 and insertion of the manipulator into hole 261. Other configurations of features are also contemplated for engaging the support structure for purposes of manipulating during placement and activation.

A feature affixed to, or integral with, the support structure can be used to selectively apply a torque or other force to generate compressive pressure on a selected portion of a ring or rings. In one example, a feature can be used for delivering energy (RF) such as for purposes of activating (bonding) or disbonding the support structure and the membrane. Features distributed about the support structure can be used for selective activation. For example, one support structure illustrated herein includes four features.

Figure 21A:
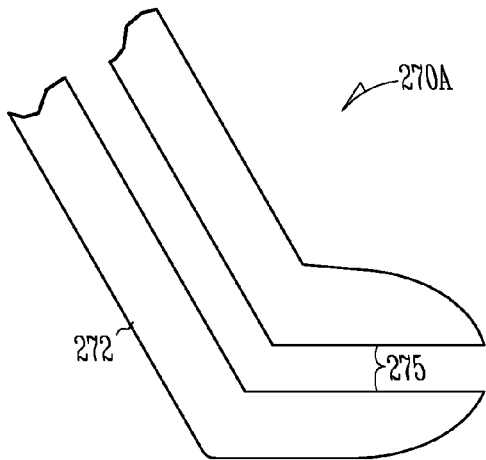
FIGS. 21A and 21B illustrate portions of a manipulator for controlling a support structure.
Figure 21B:
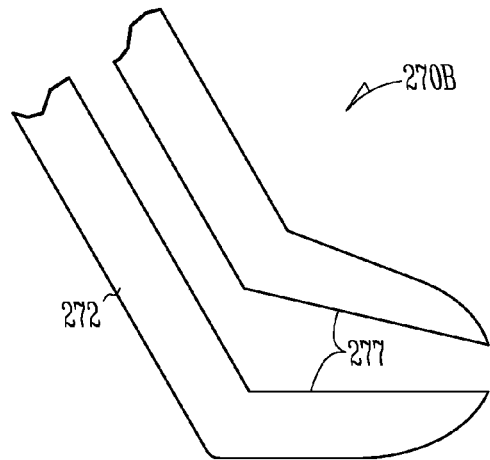

FIGS. 21A and 21B illustrate portions of exemplary manipulators suitable for use with a particular support structure. In FIG. 21A, manipulator 270A includes parallel clamping surfaces 275. In one example, the clamping surfaces travel in a linear manner and remain parallel when operated by legs 272. Legs 272 are at an angle of approximately 60-70 degrees with respect to the clamping surfaces, however other angles are also contemplated. In FIG. 21B, clamping surfaces 277 are set at an angle that causes a work piece to be clamped at a corresponding angle. For example, a support structure can be manipulated or clamped so that one portion makes contact with the membrane before another portion of the support structure. In one example, the manipulator includes a pair of forceps, a micro-manipulator or a remotely operable actuator. Forceps are a hand-held instrument used for grasping and holding an object.

Figure 22A:
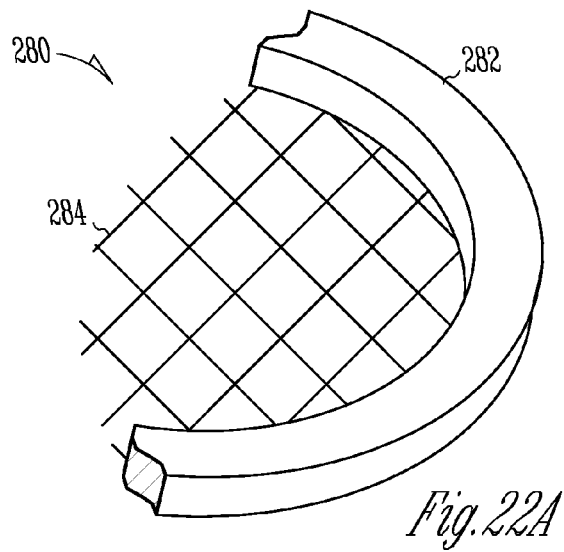
FIGS. 22A and 22B illustrate views of tissue repair structures.
Figure 22B:
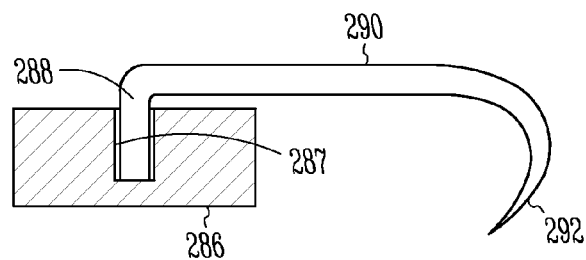

FIGS. 22A and 22B illustrate structures for keeping the membrane from being torn or for treating a torn membrane. Support structure 280 shown in FIG. 22A includes ring 282 bonded to mesh 284. Mesh 284 is affixed to a tissue contact surface of ring 282 and provides a structure that supports torn tissue disposed within the circumference of ring 282. Mesh 284 includes a biocompatible material and can include a bioerodable material, a biodegradable material, an elastic material or other substance. For tears or other damage external to the support structure, a structure as illustrated in FIG. 22B can be used. FIG. 22B illustrates ring 286 having hole 287 disposed in a surface. In the example illustrated, hole 287 is a blind hole, however, through holes can also be used. In other examples, hole 287 includes internal splines, threads, clamps or other features that engage a corresponding structure of support 290. Support 290 includes leg 288 and hook 292. Hook 292 engages a portion of tissue and exerts a force that stabilizes a torn tissue based on the fixed alignment between support 290 and ring 286. Support 290, in various examples, includes a metal or polymer structure.

Figure 23:
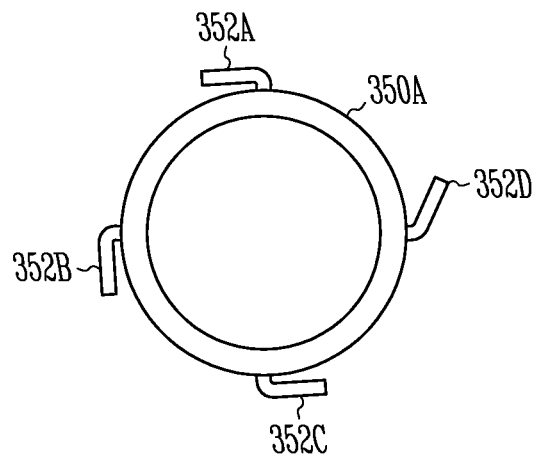
FIG. 23 illustrates a support structure having deployable features.

FIG. 23 illustrates a view of support structure 350A having a generally circular shape. As used herein, shape refers to a two-dimensional configuration when viewed from above. Support structure 350A includes a plurality of features 352A, 352B, 352C, and 352D. The features illustrated include four tabs uniformly distributed about the circumference, however, more or fewer features and different placement are also contemplated. In various examples, the features allow manipulation or activation of the support structure. In one example, the features are held in a closed or retracted position by material properties selected for the feature. For example, a shape memory material can be selected to provide a retracted position as shown by features 352A, 352B, and 352C and when activated by temperature or other energy source, the features are deployed as shown by feature 352D. Thermal energy can be provided by an external source or by natural body temperature. Radio frequency energy can be provided by a suitably configured manipulator or forceps. In one example, the features are electrically isolated from the ring of support structure 350A. An electrically isolated feature allows the surgeon to selectively bond the feature to the membrane.

In one example, a shape memory material provides a retracted position as shown by feature 352A or a partially or fully retracted position in which the feature is flush with a surface of support structure 350A. In a flush position, the feature is disposed in a cavity or channel in a manner similar to a folding blade of a pocket knife.

Figure 24:
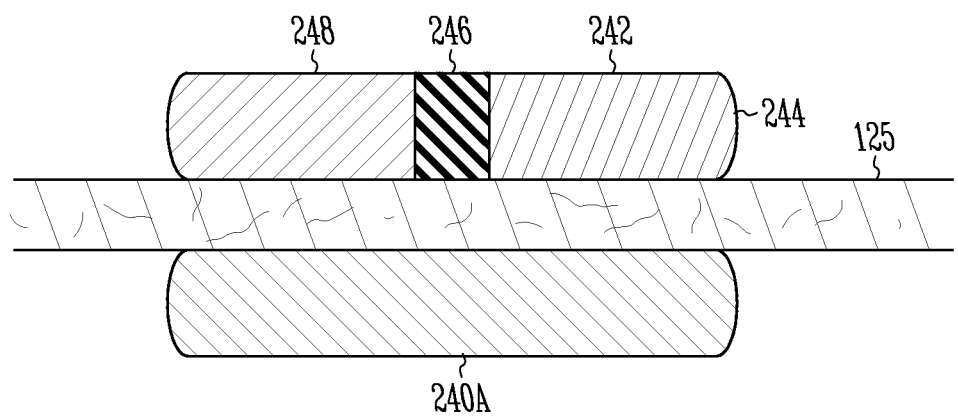
FIG. 24 illustrates a multi-element support structure.

FIG. 24 illustrates a cross section of a portion of a support structure. In the figure, the support structure includes a first ring 240A disposed on a first surface of membrane 125. A second ring 242 is disposed on a second surface of membrane 125, and in one example, the second surface includes the RPE layer. Second ring 242 includes two electrical conductors separated by an insulator or dielectric 246. The dielectric can include an oxide layer. In one example, ring 244 and ring 248 are concentric. Rings 240A, 244, and 248 are separately accessible by way of features disposed about the support structure and when energized, bond to the membrane. In particular, second ring 242 can be placed on the RPE in a manner that avoids scraping or damage to the cells on the surface of the membrane. Once placed in position, energy can be applied to the two conductors of second ring 242, thus bonding the second ring to the membrane. After placing second ring 242 in position, first ring 240A can be positioned and bonded to the membrane. First ring 240A can be activated by applying energy to one or both of ring 244 and ring 248. In various examples, second ring 242 (including ring 244, ring 248 and dielectric 246) are separate elements or of a unitary construction.

In one example, the support structure includes a single ring or other structure (configured for placement on a single side of the tissue) where the ring or other structure has a portion including two electrical conductors separated by an insulator or dielectric. For example, graduated portion 43 of the ring illustrated in FIG. 4D can include two electrically isolated conductors that can be used to apply bonding energy. As another example, tab 41 (of the ring illustrated in FIG. 4C) or tab 45 (of the ring illustrated in FIG. 4E) can include two electrically isolated conductors that can be used to apply bonding energy. This structure allows a surgeon to both manipulate the rings (+ or − pole) as well as activate the rings using an energy source such as radio frequency.

Figure 25A:
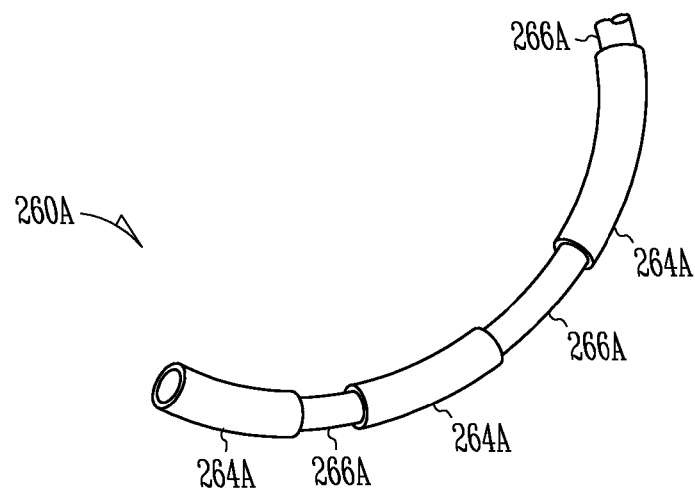
FIGS. 25A and 25B each illustrate segmented insulation of a portion of a support structure.
Figure 25B:
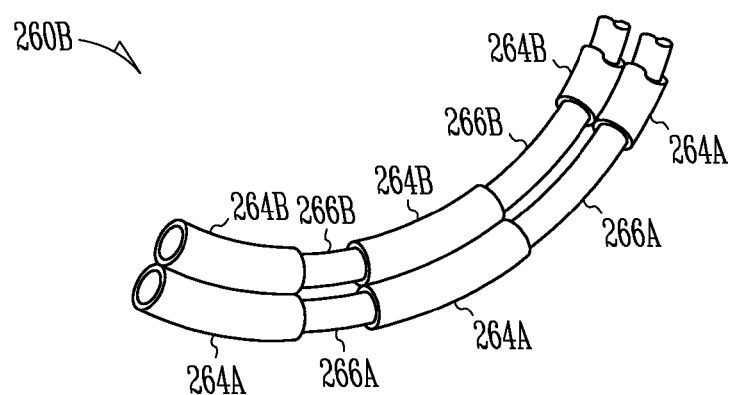

FIGS. 25A and 25B illustrate portions of support structures having segmented insulators. In FIG. 25A, electrically conductive portions of the support structure are exposed at 266A. Insulators 264A shield selected portions of the support structure. At exposed portions 266A, a bond is readily formed between the support structure and the membrane by applying monopolar RF energy. In FIG. 25B, the support structure includes a pair of adjacent electrical conductors, each having segmented insulators. In particular, electrically conductive portions of the support structure are exposed at 266A and 266B. Insulators 264A and 264B shield selected portions of the support structure. At exposed portions 266A and 266B, a bond is readily formed with the tissue disposed between the adjacent rings of the support structure by applying bipolar RF energy.

Figure 26:
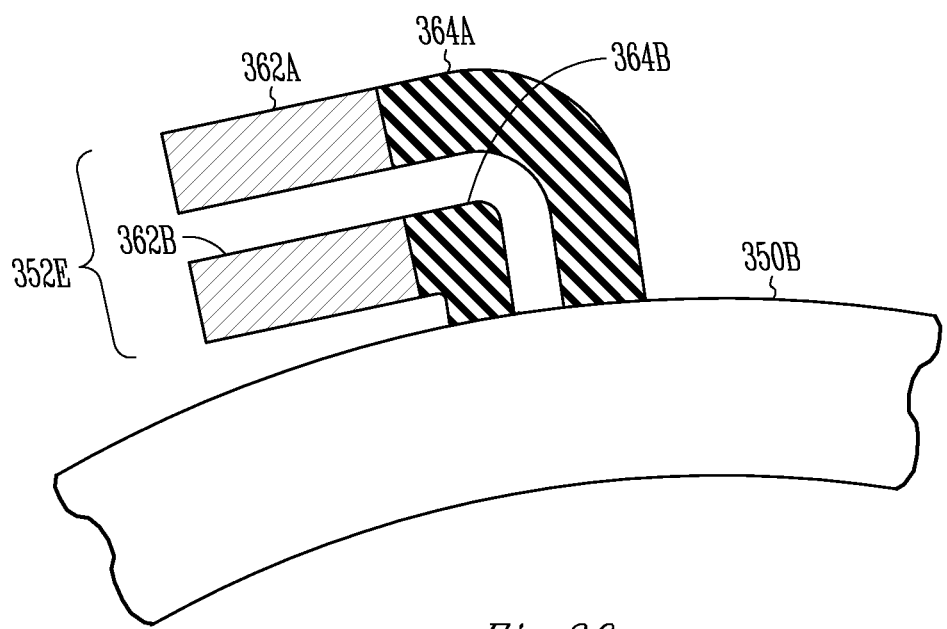
FIG. 26 illustrates a partial sectional view of a feature affixed to a support structure.

FIGS. 23, 24, and 25 exemplify various means of attaching a support structure to a tissue surface using RF energy. Other means are also contemplated and can generally be described as having two conductors, relatively closely spaced, and separated by a dielectric or insulator. In one example, the two conductors are disposed at intervals, thus forming regions where the conductors are very close. The conductors can be positioned to contact the tissue so that RF energy applied to the conductors passes through a circuit including the two conductors as well as the tissue adjacent the separating insulator. FIG. 26 illustrates a partial sectional view of an example in which a feature includes two electrically isolated conductors. Feature 352E is affixed to support structure 350B. Feature 352E includes a first electrical conductor 362A, which is isolated from the support structure by insulator 364A, and a second electrical conductor 362B, which is isolated from the support structure by insulator 364B. Bipolar RF energy can be applied to conductor 362A and conductor 362B, and when the device is in contact with tissue, a bond is formed by the current in the tissue.

Particular embodiments of the present subject matter can be used to maintain a fixed shape of the excised graft and facilitate translocation. A tissue contact surface of the support structure is bonded to the membrane and resists the tendency of the excised tissue to distort or shrink. The graft is supported by the support structure and a feature of the support structure facilitates translocating the graft along with the support structure.

In one example, the support structure remains permanently bonded to the graft after placement of the graft in the new position in the eye. In one example, the support structure is of a temporary nature and can be selectively disbonded from the graft after translocating the graft and before formation of a fibrous capsule. The graft can be disbonded by various means including application of an electric current, exposure to a chemical releasing agent or by mechanical removal.

The support structure can be configured to harvest and translocate a graft in the form of a pedicle or a circular (or other closed) shape.

The support structure can be fabricated by electrical discharge machining (EDM), by photolithography or other semiconductor fabrication technology.

Manipulation of the support structure can endanger the RPE or cause a tear or other damage. Such hazards can be mitigated by an embodiment of the present subject matter including a mesh or screen that encircles the support structure. The mesh or screen can be disposed on one or both sides of the membrane. In one example, a tool is engaged with a hole in the surface of the support structure (a through hole or a blind hole) and an end of the tool stabilizes the adjacent membrane. Retraction of the support structure would also mitigate injury to the surrounding tissues.

In one example, the support structure is configured for use on one side of the membrane. As such, the support structure is bonded to the RPE side or the choroid side of the membrane. In one example, the support structure is configured for use on two sides of the membrane and the graft is sandwiched between.

In one example, the features are used to deliver RF energy sufficient to tack the support structure to the membrane. As such, the RF energy is delivered at multiple sites (or features) distributed about the periphery. In one example, the features are electrically isolated from a main electrode and energy is selectively applied to activate particular portions. In one example, the features include isolated electrodes that are selectively deployable. In one example, the features maintain a retracted position until energized (by body temperature or above, or electrical energy) and are deployed to allow harvesting of the graft. In one example, each feature includes a two-conductor element that can be selectively bonded to underlying tissue using bipolar RF energy or laser energy.

In one example, the support structure includes a ring having a diameter of 3-5 mm.

In one example, a posterior ring of the support structure is inserted into the suprachoroidal space and an anterior ring of the support structure is placed on the RPE. The two rings are aligned with each other over the donor site. A source of RF energy is applied to the two rings which serve as electrodes. The RF energy causes the tissue to bond to the rings.

In one example, the anterior ring includes at least two separate conductors and is positioned on the RPE surface. The separate conductors of the support structure are electrically isolated and when coupled to a RF energy source, serve as electrodes to bond the anterior ring to the tissue. After bonding the anterior ring, the posterior ring is aligned and placed in position in the suprachoroidal space. This procedure may reduce the incidence of damage to the RPE surface.

The graft is carried to the translocation site by maneuvering and manipulating the support structure after excising the tissue from the membrane. In one example, the target (or translocation) site underlies the macula. Reattachment of the retina will likely hold the graft in position by the natural RPE pumping mechanism that dehydrates the subretinal space. This creates a "vacuum seal" of the graft and support ring in position. Alternatively, the graft can be held in position by tacking the support structure to the membrane at the new site. Features or other small electrode elements of the support structure can be used to fix the graft in position. The features or other small electrodes may be the same or different from those features used for affixing the support structure at the donor site. It is expected that blood vessels from the native choroid will grow into the graft, vascularize the donor tissue, and help secure the tissue in position.

In one example, the support structure includes a double ring structure. For example, an outer ring remains at the donor site, and the inner ring, which is bonded to the graft tissue, disengages from the outer ring, and is relocated to the target site. This configuration allows a compressive ring at the recipient site (to prevent shrinkage), and compression ring at the donor site (to prevent bleeding).

In one example, a bioadhesive serves as the support structure as well as a bonding agent for attachment to the graft. The bioadhesive is compatible with the body environment and can be applied to one or more tissue layers. The bioadhesive cures to a rigid or semi-rigid state and provides support for the excised graft.

In one example, the support structure is mechanically coupled to the graft. For example, a graft is disposed between a support structure having two clamping surfaces (as shown in FIGS. 19A and 19B). A mechanical clamping force sandwiches the tissue between the two surfaces. In such a configuration, the surrounding tissue is coagulated and the graft is excised without having activated the support structure. A clamping force can be described as a mechanical bond.

In one example, a manipulation tool is integrated as a unit with the support structure. As such, the manipulation tool portion is not readily separable from the support structure portion and the unit is used for both harvesting and placing of the graft after which the unit is wholly removed from the eye. For example, in particular embodiments illustrated at FIGS. 12B and 12C, the guide (tool) remains attached to the support structure.

This document discusses, among other things, a system of translocating a graft for treatment of age-related macular degeneration. Structural support devices, manipulation tools and corresponding methods are described. In the case of an external source of tissue, one method includes forming an incision to accommodate insertion of the graft.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A method of translocating a multilayer patch of tissue that includes a target, comprising:
   placing a tissue contact surface of a first support structure on a first surface of a target of a tissue, the first support structure being a structural frame having a geometric shape and including a shape memory material;
   affixing the tissue contact surface of the first support structure on the first surface of the target of the tissue; and
   separating the target affixed to the first support structure from the tissue (i) surrounding the target and (ii) the first support structure, by manipulating the first support structure;
   wherein the shape memory material includes a shape-memory metal alloy.

2. The method of claim 1, further comprising:
   positioning the target and the first support structure at a destination site within an eye of a patient; and
   affixing the target and the first support structure at the destination site.

3. The method of claim 1, further comprising:
   placing a tissue contact surface of a second support structure on a second surface of the target, the second surface opposing the first surface, the second support structure being a structural frame having a geometric shape and including a shape memory material,
   wherein the placing the second support structure includes orienting the first support structure and the second support structure in a predetermined alignment; and
   affixing the tissue contact surface of the second support structure to the second surface.

4. The method of claim 1, wherein the separating includes at least one of coagulating, ablating, and incising the tissue.

5. The method of claim 1, wherein the affixing the first support structure includes transitioning the shape memory material from a first configuration to a second configuration.

6. The method of claim 1, wherein the affixing includes bonding the tissue contact surface of the first support structure to the first surface of the tissue.

7. The method of claim 6, wherein:
   the bonding includes applying energy to the first support structure; and
   the applying energy includes applying at least one of radio frequency energy, thermal energy, optical energy, and electrical energy.

8. The method of claim 1,
   wherein the structural frame has a circular shape having a center; and
   wherein the target is disposed in the center of the structural frame.

9. The method of claim 8, wherein
   the tissue contact surface includes a textured surface.

10. The method of claim 1, wherein the tissue includes choroid, Bruch's membrane, and RPE.

11. A method of translocating a tissue graft, comprising:
    placing a tissue contact surface of a support structure on a surface of a tissue, the support structure including a structural frame having a geometric shape and including a shape memory material;
    bonding the tissue contact surface of the support structure to the surface of the tissue;
    separating (i) the tissue bonded to the support structure and (ii) the support structure from the tissue surrounding the support structure to form a graft; and
    manipulating the support structure to reposition the graft to a destination site;
    wherein the shape memory material includes a shape-memory metal alloy.

12. The method of claim 11, wherein the bonding includes at least one of forming a chemical bond or applying radio frequency (RF) energy.

13. The method of claim 12, wherein the forming the chemical bond includes using an adhesive.

14. The method of claim 13, further comprising:
    selectively disbonding the support structure from the surface of the tissue,
    wherein the selectively disbonding includes at least one of bioeroding and laser ablating.

15. The method of claim 11, wherein the manipulating includes at least one of engaging a feature of the support structure or exerting a torque on the support structure.

16. The method of claim 11,
    wherein the structural frame has a circular shape having a center; and
    wherein the target is disposed in the center of the circular shape of the structural frame.

17. The method of claim 16, wherein the tissue includes choroid, Bruch's membrane, and retinal pigment epithelium (RPE).

18. The method of claim 16, wherein
    the tissue contact surface includes a textured surface.

19. A method of preparing a graft of eye tissue for translocation, comprising:
    bonding a tissue contact surface of a first support structure to a first surface of a target on a tissue so that the target is encircled by the first support structure, the first support structure being a ring and including a shape memory material; and
    separating (i) the target bonded to the support structure and (ii) the first support structure from the tissue surrounding the first support structure to form a graft,
    wherein the tissue includes choroid, Bruch's membrane, and retinal pigment epithelium (RPE).

20. The method according to claim 19, further comprising:
    bonding a tissue contact surface of a second support structure to a second surface of the target, the second surface opposing the first surface,
    wherein the second support structure is a ring and includes a shape memory material, and
    wherein the separating includes separating the target bonded to the first support structure and the second support structure, the first support structure, and the second support structure from the tissue surrounding the first support structure and the second support structure.

21. The method of claim 19, wherein:

the shape memory material includes a shape-memory metal alloy; and the tissue contact surface includes a textured surface.

* * * * *